US010512699B2

(12) United States Patent
Koronyo et al.

(10) Patent No.: US 10,512,699 B2
(45) Date of Patent: *Dec. 24, 2019

(54) OPTICAL METHOD FOR THE DETECTION OF ALZHEIMER'S DISEASE USING CURCUMIN

(71) Applicants: Cedars-Sinai Medical Center, Los Angeles, CA (US); Yeda Research and Development Co., Ltd., Rehovot (IL)

(72) Inventors: Yosef Koronyo, Los Angeles, CA (US); Maya Koronyo, Los Angeles, CA (US); Keith Black, Los Angeles, CA (US); Michal Schwartz, Rehovot (IL); Daniel L. Farkas, Los Angeles, CA (US)

(73) Assignees: Cedars-Sinai Medical Center, Los Angeles, CA (US); Yeda Research and Development Co., Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/798,612

(22) Filed: Oct. 31, 2017

(65) Prior Publication Data
US 2019/0022255 A1 Jan. 24, 2019

Related U.S. Application Data

(63) Continuation of application No. 13/119,596, filed as application No. PCT/US2009/057569 on Sep. 18, 2008, now Pat. No. 9,839,699.

(60) Provisional application No. 61/098,206, filed on Sep. 18, 2008.

(51) Int. Cl.
| | |
|---|---|
| A61B 5/00 | (2006.01) |
| A61B 3/00 | (2006.01) |
| A61B 6/00 | (2006.01) |
| A61K 49/00 | (2006.01) |
| A61K 31/404 | (2006.01) |
| A61K 31/4965 | (2006.01) |
| A61K 31/5377 | (2006.01) |
| A61K 31/496 | (2006.01) |
| A61K 31/437 | (2006.01) |
| G01N 33/50 | (2006.01) |
| A61B 3/10 | (2006.01) |
| A61B 3/14 | (2006.01) |

(Continued)

(52) U.S. Cl.
CPC ........ *A61K 49/0021* (2013.01); *A61K 49/006* (2013.01); *A61B 3/0025* (2013.01); *A61B 3/102* (2013.01); *A61B 3/14* (2013.01); *A61B 5/4088* (2013.01); *A61B 5/7264* (2013.01); *A61B 6/037* (2013.01); *A61B 6/506* (2013.01); *A61K 31/404* (2013.01); *A61K 31/437* (2013.01); *A61K 31/496* (2013.01); *A61K 31/4965* (2013.01); *A61K 31/5377* (2013.01); *A61K 49/0004* (2013.01); *A61K 49/0032* (2013.01); *A61K 49/0056* (2013.01); *C07D 401/14* (2013.01); *G01N 33/5008* (2013.01); *G01N 33/5082* (2013.01); *G01N 33/5091* (2013.01); *G01N 2333/4709* (2013.01); *G01N 2800/28* (2013.01); *G01N 2800/2821* (2013.01); *G01N 2800/52* (2013.01)

(58) Field of Classification Search
CPC ......... A61B 3/102; A61B 3/12; A61B 3/1208; A61B 3/14; A61B 5/0066; A61B 2576/026; A61B 3/10; A61B 3/13; A61B 5/0042; A61B 5/0071; A61B 5/4064; A61K 49/0021; A61K 31/4965; A61K 31/55; A61K 49/0066; A61K 49/006; A61K 51/04; A61K 51/088; A61K 9/0019; A61K 9/0085; G01N 33/6896; G01N 2500/04; C12Q 1/6883; C12Q 2600/158; C12Q 2600/12; C07K 14/4711; C12N 5/0619
See application file for complete search history.

(56) References Cited

U.S. PATENT DOCUMENTS

| | | |
|---|---|---|
| 5,987,351 A | 11/1999 | Chance |
| 6,013,034 A | 1/2000 | Fernandes Da Cunha Vaz et al. |
| 6,198,532 B1 | 3/2001 | Cabib et al. |

(Continued)

FOREIGN PATENT DOCUMENTS

| | | |
|---|---|---|
| WO | WO 2003/018068 | 3/2003 |
| WO | WO 2002/016951 | 2/2008 |
| WO | WO 2010/017094 | 2/2010 |

OTHER PUBLICATIONS

Perez et al. Invest. Ophthalmol. Vis. Sci. published online Sep. 12, 2008, 2009; 50:793-800.*
Vickers, Australian and New Zealand J. of Ophthalmol., 1997; 25:105-109.*
Garcia-Alloza et al., J. Neurochem., 2007; 102:1095-1104.*
Wang et al. ARch Ophthalmol. 2009; 127:875-881.*
Anand et al. Molecular. Pharmaceutics, 2007, 4:807-818.
Yang et al. J. Biol. Chem., 2005; 280:5892-5901.
LeVine Ana. Biochem. 2006; 356: 265-272.

(Continued)

*Primary Examiner* — Chang-Yu Wang
(74) *Attorney, Agent, or Firm* — Law Offices of Alan J. Morrison

(57) ABSTRACT

The present subject matter relates to a non-invasive optical imaging method for monitoring early pathological events specific to Alzheimer's disease (AD), such as the development, amount and location of amyloid plaques. The ability to monitor such events provides a basis for, among other things, AD diagnosis, prognosis and assessment of potential therapies. In addition, the present subject matter introduces novel methods for treating AD and retinal ailments associated with AD. Aβ-plaque detection in living brains is extremely limited, especially at high resolution; therefore the present invention is based on studies focusing on the eyes as an alternative to brain-derived tissue that can be imaged directly, repetitively and non-invasively.

20 Claims, 17 Drawing Sheets

(51) Int. Cl.
*A61B 6/03* (2006.01)
*C07D 401/14* (2006.01)

(56) References Cited

U.S. PATENT DOCUMENTS

| | | | |
|---|---|---|---|
| 6,274,119 | B1 | 8/2001 | Barrio et al. |
| 6,660,530 | B2 | 12/2003 | Barrio et al. |
| 7,107,092 | B2 * | 9/2006 | Goldstein ............ A61B 5/0059 |
| | | | 351/214 |
| 7,341,709 | B2 | 3/2008 | Barrio et al. |
| 7,575,321 | B2 | 8/2009 | Newman et al. |
| 7,653,428 | B2 | 1/2010 | Goldstein et al. |
| 7,678,819 | B2 | 3/2010 | Kung et al. |
| 7,700,616 | B2 | 4/2010 | Tamagnan et al. |
| 7,799,808 | B2 | 9/2010 | Cheng et al. |
| 7,854,510 | B2 | 12/2010 | Verdooner et al. |
| 8,318,132 | B2 | 11/2012 | Kolb et al. |
| 8,372,380 | B2 | 2/2013 | Barrio et al. |
| 9,730,580 | B2 | 8/2017 | Verdooner |
| 9,808,155 | B2 | 11/2017 | Verdooner |
| 9,839,699 | B2 * | 12/2017 | Koronyo ............ A61K 49/006 |
| 2002/0022002 | A1 | 2/2002 | Barrio et al. |
| 2002/0091321 | A1 | 7/2002 | Goldstein et al. |
| 2002/0182152 | A1 * | 12/2002 | Goldstein .......... A61K 49/0021 |
| | | | 424/9.6 |
| 2004/0072371 | A1 | 4/2004 | Barrio et al. |
| 2004/0152068 | A1 | 8/2004 | Goldstein et al. |
| 2004/0167217 | A1 | 8/2004 | Scapagnini et al. |
| 2004/0192588 | A1 | 9/2004 | Eisenbach-Schwartz et al. |
| 2006/0025658 | A1 | 2/2006 | Newman et al. |
| 2007/0053831 | A1 | 3/2007 | Barrio et al. |
| 2007/0060644 | A1 | 3/2007 | Vander Jagt et al. |
| 2009/0041666 | A1 | 2/2009 | Goldstein et al. |
| 2009/0123373 | A1 | 5/2009 | Wang et al. |
| 2009/0304591 | A1 | 12/2009 | Russmann et al. |
| 2011/0046378 | A1 | 2/2011 | Kolb et al. |
| 2011/0234977 | A1 | 9/2011 | Verdooner |

OTHER PUBLICATIONS

PCT/US09/57569 ISR and Written Opinion dated Nov. 19, 2009.
Xie Zhao-yang, et al., Chinese Journal of New Drugs, 2007, vol. 16 No. 1, pp. 36-40.
Koronyo et al., "Noninvasive Optical Imaging of Retinal Amyloid Plaques in Mice Model of Alzheimer's disease: Early Detection and Treatment Assessment," alzheimer's association, Abstract, 3 pages (2010).
Koroyno et al., "Optical imaging of amyloid plaques in the retina for Alzheimer's disease detection and treatment assessment," Neuroscience 2009, Abstract, 2 pages (2009).
Koroyno et al. "Noninvsive Optical Imaging of .beta.-Amyloid Plaques in Live AD Mice Retina and Identification of A.beta. Plaques in Postmortem Retinas from Human AD Patients," Poster # P3-188, Abstract Control #2932, Cedar-Sinai Medical Center (2009).
Koroyno et al., In Vivo Optical Imaging of Retinal Amyloid Plaques in Mice Model of Alzheimer's disease: Early Detection and Treatmet Assessment, Poster #12, Abstract, Cedar-Sinai Medical Center (2009).
Frenkel et al., "Nasal vaccination with a proteasome-based adjuvant and glatiramer acetate clears .beta.-amyloid in a mouse model of Alzheimer disease," The Journal of Clinical Investigation, vol. 115, No. 9, pp. 2423-2433 (2005).
Guo et al., "Targeting amyloid-.beta. in glaucoma treatment," Proc. National Academy of Science, vol. 104, No. 33, pp. 13444-13449 (2007).
Goldstein et al., "Cytosolic .beta.-amyloid deposition and supranuclear cataracts in lenses from people with Alzheimer's disease," The Lancet, vol. 361, No. 9365, pp. 1258-1265 (2003).
Perez et al., ".beta.-Amyloid Deposition and Functional Impairment in the Retina of the APPswe/PS1.DELTA.E9 Transgenic Mouse Model for Alzheimer's Disease," Investigative Ophthalmology & Visual Science, vol. 50, No. 2, pp. 793-800 (2008).
Shimazawa et al., "Reduced retinal function in amyloid precursor protein-over-expressing transgenic mice via attenuating glutamate-N-methyl-D-asparatate receptor signaling," Journal of Neurochemistry, vol. 107, No. 1, pp. 279-290 (2008).
Ning et al., "Amyloid-.beta. Deposits Lead to Retinal Degeneration in a Mouse Model of Alzheimer Disease,"Investigative Ophthalmology & Visual Science, vol. 49, No. 11, pp. 5136-5143 (2008).
Sharifzadeh et al., "Resonance Raman imaging of macular pigment distrubutions in the human retina," Journal of the Optical Society of America, vol. 25, No. 4, pp. 947-957 (2008).
Yang et al., "Curcumin Inhibits Formation of Amyloid .beta. Oligomers and Fibrils, Binds Plaques, and Reduces Amyloid in Vivo," Journal of Biological Chemistry, vol. 280, No. 7, pp. 5892-5901 (2005).
Koronyo-Hamaoui et al., "Identification of amyloid plaques in retinas from Alzheimer's patients and noninvasive in vivo optical imaging of retinal plaques in a mouse model," NeuroImage, vol. 54, pp. 5204-5217 (2011).
Hinton, D.R., et al., "Optic-nerve degeneration in Alzheimer's disease", N Engl J Med. Aug. 21, 1986;315(8)485-7 (Abstract only).
Blanks, J.C., et al., "Retinal ganglion cell degeneration in Alzheimer's disease", Brain Res. Nov. 6, 1989;501(2):364-72 (Abstract only).
M.L. Ford and B.D. Evavold, "An MHC anchor-substituted analog of myelin oligodenrocyte glycoprotein 35-55 induces IFN-.gamma. and autoantibodies in the absence of experimental autoimmune encephalomyelitis and optic neuritis", Eur. J. Immunol., 2004, 34:388-397.
L.E. Goldstein, et al., "Cytosolic .beta.-amyloid deposition and supranuclear cataracts in lenses from people with Alzheimer's disease", Lancet 2003; 361: 1258-65.
Anand, et al., "Bioavailability of Curcumin: Problems and Promises", Mol. Pharmaceutics, 2007, 4 (6), 807-818.
Mannermaa, et al., "Drug transport in corneal epithelium and blood-retina barrier: emerging role of transporters in ocular pharmacokinetics", Adv Drug Deliv Rev. Nov. 15, 2006;58(11):1136-63. Epub Sep. 16, 2006. (Abstract Only).
Hosoya, et al., "Vitamin C transport in oxidized form across the rat blood-retinal barrier", Invest Ophthalmol Vis Sci. Apr. 2004;45(4):1232-9.
Zsila, et al., "Circular dichroism spectroscopic studies reveal pH dependent binding of curcumin in the minor groove of natural and synthetic nucleic acids", Org Biomol Chem. Oct. 21, 2004;2(20):2902-10. Epub Sep. 23, 2004. (Abstract Only).
Zsila, et al., "Induced circular dichroism spectra reveal binding of the antiinflammatory curcumin to human alpha1-acid glycoprotein", Bioorg Med Chem. Jun. 15, 2004;12(12):3239-45. (Abstract Only).
Gupta, et al., "Dietary antioxidant curcumin inhibits microtubule assembly through tubulin binding", FEBS J. Dec. 2006;273(23):5302-32. Epub Oct. 26, 2006. (Abstract Only).
Barik, et al., "Photophysical studies on binding of curcumin to bovine serum albumins", Photochem Photobiol. Jun. 2003;77(6):597-603. (Abstract Only).
Reinke, A. A. and Gestwicki, J. E. (2007), Structure-activity Relationships of Amyloid Beta-aggregation Inhibitors Based on Curcumin: Influence of Linker Length and Flexibility. Chemical Biology & Drug Design, 70: 206-215. (Abstract Only).
L.C. Serpell, "Alzheimer's amyloid fibrils: structure and assembly", Biochimica et Biophysica Acta, 1502:16-30 (2000).
B. O'Nuallain and R. Wetzel, "Conformational Abs Recognizing a Generic Amyloid Fibril Epitope", PNAS, vol. 99, No. 3, pp. 1485-1490 (2002).
T. Cavallero, et al., "The Retinal Pigment Epithelium Is the Unique Site of Transthyretin Synthesis in the Rat Eye", Investigative Ophthalmology & Visual Science, vol. 31, No. 3, pp. 497-501, Mar. 1990.
P.M. Martin, et al., "Expression and Polarized Localization of the Hemochromatosis Gene Product HFE in Retinal Pigment Epithelium", Investigative Ophthalmology & Visual Science, vol. 47, No. 10, pp. 4238-4244, Oct. 2006.

(56) References Cited

OTHER PUBLICATIONS

G. Cancel, et al., "Distribution of Ataxin-7 in Normal Human Brain and Retina", Brain, 123:2519-2530, 2000.

P.P.N. Rao, et al., "Curcumin Binding to Beta Amyloid: A Computational Study", Chemical Biology & Drug Design, 2015, 86:813-820.

J.-D. Ding, et al., "Targeting age-related macular degeneration with Alzheimer's disease based immunotherapies: Anti-amyloid-.beta. antibody attenuates pathologies in an age-related macular degeneration mouse model", Vision Research 48 (2008) 339-345.

M. Shimazawa, et al., "Reduced retinal function in amyloid precursor protein-over-expressing transgenic mice via attenuating glutamate-N-methyl-D-aspartate receptor signaling", J. of Neurochemistry, 2008, 107:279-290.

A. Ning, et al., "Amyloid-.beta. Deposits Lead to Retinal Degeneration in a Mouse Model of Alzheimer Disease", Investigative Ophthalmology & Visual Science, Nov. 2008, vol. 49, No. 11, 5136-5143.

N. Okamura, et al., "In Vivo Imagining of Amyloid Plaques", Folia Pharmacol. Jpn., (2008) 131:333-337 [Japanese language reference with English language abstract].

* cited by examiner

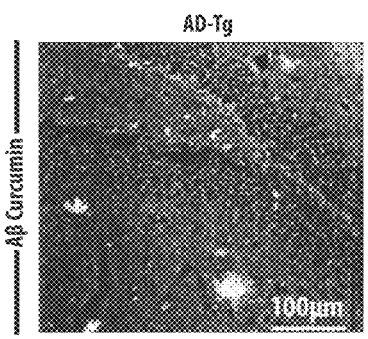
Fig. 1a
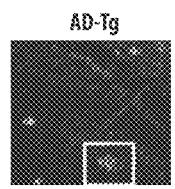 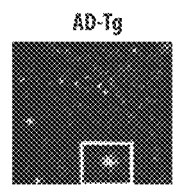
Fig. 1b    Fig. 1c
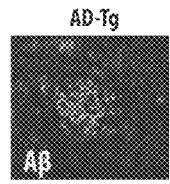 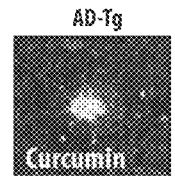
Fig. 1d    Fig. 1e
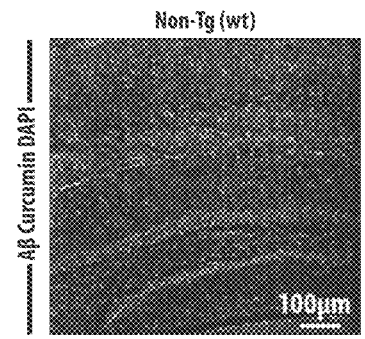
Fig. 1f

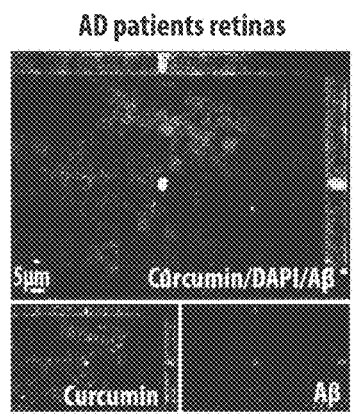
Fig. 2k
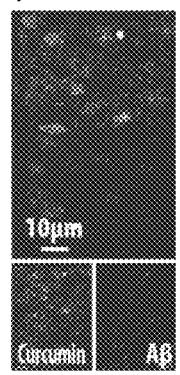     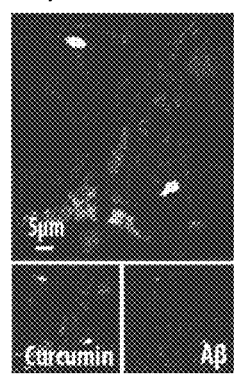
Fig. 2l           Fig. 2m
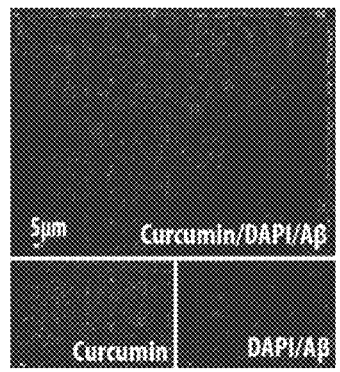
Fig. 2n

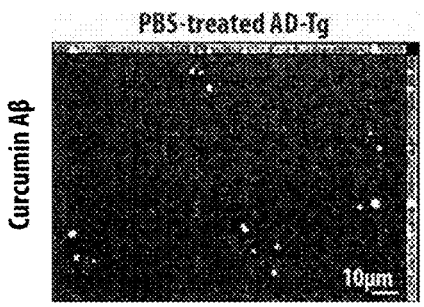
Fig. 4a
   
Fig. 4b            Fig. 4c
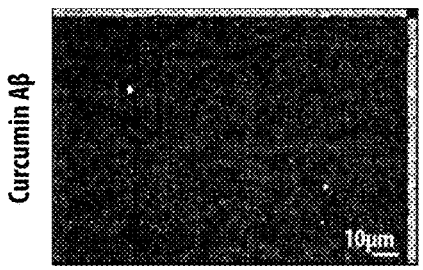
Fig. 4d
   
Fig. 4e            Fig. 4f
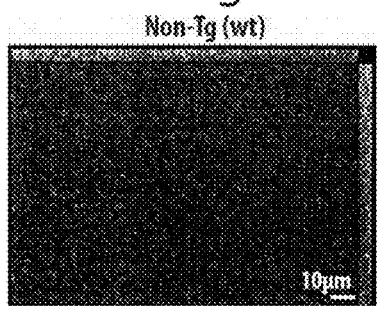   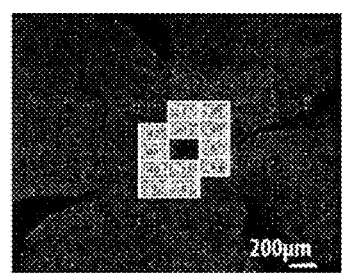
Fig. 4g            Fig. 4h i.v. Curcumin i.v. PBS i.v. Curcumin i.v. Curcumin i.v. Curcumin & OS

OPTICAL METHOD FOR THE DETECTION OF ALZHEIMER'S DISEASE USING CURCUMIN

PRIORITY DATA

This application is a continuation of U.S. application Ser. No. 13/119,596, filed Jul. 22, 2011, which is a § 371 national stage entry of PCT Application No. PCT/US2009/057569, filed Sep. 18, 2009, which claims priority of U.S. Provisional Application No. 61/098,206, filed Sep. 18, 2008, the entire disclosures of which are incorporated herein by reference.

FIELD OF THE SUBJECT MATTER

The present subject matter relates to methods for noninvasive monitoring of early pathological events specific to Alzheimer's disease, and thus includes methods and systems for the diagnosis, treatment, prognosis and evaluation of response to treatment of AD.

BACKGROUND OF THE SUBJECT MATTER

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Alzheimer's disease (AD) is a common and devastating age-dependent neurodegenerative disease. AD brain pathology is characterized by typical accumulation of proteolytic products of the amyloid precursor protein (APP), amyloid-β peptides (Aβ), which form extracellular aggregates termed Aβ plaques. These plaques are believed to contribute to disrupted cellular activities and communication in the brain, leading to neurotoxic inflammation and neuronal death [2,3]. Molecular imaging, which allows a non-invasive monitoring of pathological processes in living subjects, has the potential to enhance detection and understanding of disease and drug effectiveness. Accordingly, major efforts have been invested in developing tools to enable noninvasive detection of amyloid plaques through the skull of living AD patients and animal models [4-9]; however, noninvasive monitoring of amyloid plaques is still clinically challenging and of limited availability at high resolution [10-12]. Optical imaging constitutes a powerful, high-resolution and specific tool for in vivo imaging, as recently demonstrated using multiphoton microscopy to image Aβ plaques in vivo in the mouse brain via a cranial window [13]. The present subject matter poses an alternative and noninvasive approach in humans to image the retina of AD patients by optical modalities, provided that Aβ plaques develop in these patients' retinas and share similar properties with those in the brain.

APP is widely expressed in the retinal ganglion cells (RGCs), an outgrowth of the central nervous system (CNS), and is transported to the axonal plasma membrane and the nerve terminals via the optic nerve [14]. Formation of plaques in the retina came recently under investigation, especially in two related neurodegenerative disorders: aged-related macular degeneration (AMD) and glaucoma [50-53]. It was unclear whether Aβ-plaques are found in the retina in early or late stage of AD patients. Past evidence pointed to the presence of Aβ-plaques in retinas of glaucoma and AMD patients and their rodent models. For example, Aβ deposition in the RGC layer has been reported in glaucoma patients [50, 51]. In experimental models of glaucoma, apoptosis of RGCs has been associated with the accumulation of Aβ-peptides, and agents targeting their formation were shown to exert neuroprotective activity [52]. In AMD patients, Aβ deposits were found in drusen that correlated with the location of degenerating photoreceptors and retinal pigment epithelium cells [53].

In a *Drosophila* transgenic model of AD, based on the targeted expression of mutated human APP and presenilin (PS) genes, Aβ immunoreactivity was found in the compound eye, and in association with retinal photoreceptor degeneration [15]. A recent study demonstrated Aβ deposits in the retinal nerve fiber layer (NFL) and ganglion cell layer (GCL) in AD transgenic mice at an advanced stage of the disease (later than 10 months of age). The Aβ deposits were further correlated with neurodegeneration of the RGCs and with microglial activation [16].

Despite this encouraging research, there remains a need in the art for systems and methods for the diagnosis, prognosis and treatment of AD. The present subject matter meets these needs by discovering the presence of Aβ plaques in retinas of postmortem eyes of AD patients. Using mice expressing mutated forms of the human APP and PS1 genes (APPswe/PS1dE9, referred to here as AD-Tg mice), the present subject matter also provides evidence disclosing the early formation of Aβ plaques in the retina prior to their manifestation in the brain. Furthermore, the present subject matter identifies an immune-based therapy, using a weak agonist of a myelin-derived peptide loaded on dendritic cells [17, 18], effective in reducing Aβ plaques in the mouse brains and retinas of AD-Tg mice. Finally, the subject matter demonstrated that systemic injection of curcumin (diferuloylmethane), a natural compound that binds and labels Aβ plaques [19, 20], into live animals allows for non-invasive high-resolution and specific visualization of Aβ plaques in the retina. The present subject matter teaches methods that, for the first time, allow for Aβ plaques to be detected by number and location, and be repeatedly counted and monitored in real-time in the retina of AD mammals.

BRIEF DESCRIPTION OF THE FIGURES

Exemplary embodiments are illustrated in referenced figures. It is intended that the embodiments and figures disclosed herein are considered illustrative rather than restrictive.

FIGS. 1a through 1n depict retinal Aβ deposition in the retina of AD-Tg mice visualized by curcumin. FIGS. 1a-1f depict images of brain cryosections from 9-month-old AD-Tg (FIGS. 1a-1e) and non-Tg (wt) (FIG. 1f) mice stained with anti-human Aβ antibody and curcumin ex vivo, indicating co-localization of Aβ plaque staining by both detection methods. FIGS. 1d and 1e depict higher magnification images of plaque staining pattern presented for each channel FIG. 1f shows no evidence for double-positive anti-human Aβplaques and curcumin in the non-Tg (wt) mouse. Cell nuclei were labeled with DAPI (blue). Scale bar=100 μm. FIG. 1g depicts IPL-Inner Plexiform Layer, FIG. 1h depicts INL-Inner Nuclear/OPL-Outer Plexiform Layers, and FIG. 1*i* depicts ONL-Outer Nuclear Layer. FIG. 1*j* shows Aβ plaques were essentially absent in the non-Tg (wt) mice. (FIGS. 1*g* and 1*j*, lower row). Higher magnification images for separate channels demonstrate plaque-staining patterns with both procedures. Scale bars=5 μm. FIGS. 1*k*-1*n* depict whole eye sagittal cryosections stained with curcumin in vivo, followed by anti-human Aβ antibody and DAPI ex vivo. In FIGS. 1*k*-1*m*, Aβ plaques were detected in most retinal layers and in the choroid in 10-month-old AD-Tg mice. In FIG. 1*n*, Aβ plaques were undetectable in the retina and choroid of non-Tg (wt) mice. Scale bar=20 μm.

FIGS. 2*a* through 2*n* depict Aβ plaques in the human retina of Alzheimer's disease patients. FIGS. 2*a* and 2*b* are representative images of the human whole-mount retina of an 87-yr-old AD patient after staining with Sudan Black B to eliminate non-specific autofluorescence signals, and following curcumin ex vivo staining (curcumin-labeled plaques are indicated by white arrows). Scale bars=10 μm. Cell nuclei are labeled with DAPI (blue). FIG. 2*i* represents a higher magnification image of the retinal plaque. Aβ plaque morphology was similar to that found in the mouse retinas and brains. Scale bars=5 μm. FIGS. 2*k*-2*m* represent subsequent staining of the same human retinas with curcumin, which reveals that the plaques were selectively colabeled with human Aβ antibodies and curcumin (lower row images for separate channels). FIG. 2*n* depicts double staining with human Aβ antibodies and curcumin in postmortem non-AD human retinal whole mount showing no signs of Aβ plaques (lower row images for separate channels). Scale bars=5 μm.

FIGS. 3*a*-3*n* are representative z-axis projection images of whole-mount retinas from AD-Tg (n=18) and non-Tg (wt; n=10) mice at various ages; FIGS. 3*a*-3*d* depict 2.5-month-old AD-Tg mouse, with FIG. 3*a* showing presence of plaques in the retina and FIG. 3*b* showing validation of Aβ plaque staining using specific anti-human antibody ex vivo at the same location (co-localization of curcumin and Aβ antibody in yellow). Scale bars=10 μm. FIGS. 3*c* and 3*d* show no plaques were detected in the brain hippocampus and cortex. Scale bars=100 μm. FIGS. 3*g* and 3*h* show detection of plaques in the brain. Scale bars=50 μm. FIGS. 3*l*-3*n* depict 17-month-old AD-Tg mouse, with FIG. 3*l* showing numerous plaques in the retina and FIGS. 3*m* and 3*n* showing plaques in the brain. Scale bars (i)=10 μm and (m,n)=100 μm. FIGS. 3*o*-3*q* depicts 9-month-old non-Tg (wt) mouse, with FIG. 3*o* showing no plaques in the retina and FIGS. 3*p* and 3*q* showing no plaques in the brain. Scale bars (o)=10 μm and (p,q)=100 μm.

FIGS. 4*a* through 4*k* depict decreased Aβ plaques in the retina of AD-Tg mice following dendritic cell-based vaccination. FIGS. 4*a*-4*g* are representative z-axis projection images of whole-mount retinas from 10 month-old mice, FIGS. 4*a*-4*c* show PBS-treated AD-Tg mouse control, FIGS. 4*d*-4*f* show vaccinated AD-Tg mouse, and FIG. 4*g* shows non-Tg (wt) mouse stained ex vivo with curcumin and anti-human Aβ antibodies. FIGS. 4*b* and 4*c*, and FIGS. 4*c* and 4*f* depict separate channel images for curcumin and anti-Aβ antibodies labeling in the retina. Scale bars=10 μm. FIG. 4*h* is an illustration of 12 regions around the optic disc (indicated by rectangles 1-12) representing the area covered for quantitative analyses of plaques in the retinal whole-mounts (n=4 mice per group; two retinas per mouse). Scale bar=200 μm. FIG. 4*i* depicts the decrease in plaque number, observed in the retinas of AD-Tg mice treated with immunebased vaccination as compared to PBS-treated controls (Student's t-test; P=0.0028). FIG. 4*j* depicts a decrease in mean plaque area, observed in the retinas of vaccinated AD-Tg mice as compared to their controls (Student's t-test P=0.0002). FIG. 4*k* shows that the significant reduction in the total area covered by plaques was also detected in the brain hippocampus and cortex of the same mice following immune-based vaccination (Student's t-test P=0.0085). Error bars in each panel represent SEM.

FIGS. 5*a*-5*c* are representative z-axis projection images taken from retinal whole-mounts of non-perfused AD-Tg versus non-Tg (wt) mice (10-month-old), following i.v. curcumin or PBS administration in vivo (blood vessels are indicated by red arrows). FIG. 5*a* shows Aβ plaques were visible (indicated by white arrows) in AD-Tg mouse retinas following i.v. injection of curcumin (n=6). FIG. 5*b* shows plaques were undetectable in the retinas of AD-Tg mice after i.v. injection of PBS (n=5). FIG. 5*c* shows plaques were undetectable in the retinas of non-Tg (wt) mice following i.v. injection of curcumin (n=5). FIG. 5*d* is a representative confocal z-axis projection image, using three channels and sagittal/coronal virtual sections, demonstrating Aβ plaques (plaques inside the vessels indicated with white arrows), stained with anti-human Aβ antibodies, in the parenchyma and inside the blood vessels of AD-Tg mouse retinal whole-mount. FIGS. 5*e* and 5*f* depict images captured using a fluorescence microscope with AOTF-based spectral imaging system, and analyzed and visualized by segmentation and classification software. In FIG. 5*e*, Aβ plaques (in white) and blood vessels (indicated by arrows), were visible in a retinal whole-mount stained in vivo with curcumin and imaged at a single channel (ex. 562/40 nm; em. 624/40 nm). FIG. 5*f* depicts a spectrally-classified image using optical signature (OS) specific to Aβ plaques labeled with curcumin in the same retinal whole-mount and region. Aβ plaques are shown in pseudocolor (indicated by white arrows) and all non-plaque tissue is in green pseudocolor. Scale bars=10 μm. FIGS. 5*g*-5*j* are images following a single injection of curcumin, wherein plaques (indicated with white arrows) were visible in live AD-Tg mouse retinas (n=4) by emission of light following excitation with a spectrally controlled source (wavelength of 546/15 nm). FIGS. 5*i* and 5*j* are higher magnification images, where plaques were mostly detected in areas close to the optic disc and the average plaque size was compatible with that observed in the wholemount retinas (ex vivo). FIG. 5k shows no plaques detected in the non-Tg (wt) mice (n=4) i.v. injected with curcumin. Scale bars (g, k)=100 µm, and (h-j)=10 µm. 23.

FIG. 8a (curcumin), FIG. 8b (mouse Aβ), FIG. 8c (DAPI) and FIG. 8d (Merged).

DETAILED DESCRIPTION OF THE INVENTION

Figure 1G:
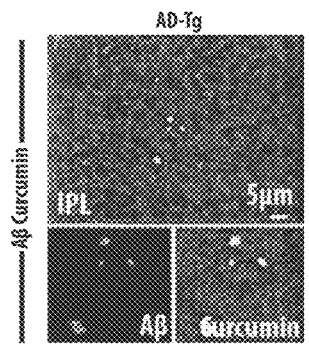
FIGS. 1g-1j are representative images of retinal whole-mounts from 10-month-old AD-Tg (n=27) and non-Tg (wt) mice (n=18) stained with anti-Aβ antibody and curcumin ex vivo. The formation of Aβ plaques (yellow spots of overlapping red and green channels) is demonstrated in several different retinal layers.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed, J. Wiley & Sons (New York, N.Y. 2001); March, Advanced Organic Chemistry Reactions, Mechanisms and Structure $5^{th}$ ed., J. Wiley & Sons (New York, N.Y. 2001); and Sambrook and Russel, Molecular Cloning: A Laboratory Manual 3rd ed, Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Administering" and/or "Administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods know in the art. Parenteral refers to a route of administration that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Alzheimer's Disease" as used herein refers to all form of dementia, identified as a degenerative and terminal cognitive disorder. The disease may be static, the result of a unique global brain injury, or progressive, resulting in long-term decline in cognitive function due to damage or disease in the body beyond what might be expected from normal aging.

"Age-related macular degeneration" as used herein refers to is a medical condition in older adults that results in a loss of vision in the center of the visual field (the macula) due to damage to the retina.

"Cataracts" as used herein refers to a clouding that develops in the crystalline lens of the eye or in its envelope, varying in degree from slight to complete opacity and obstructing the passage of light. Early in the development of age-related cataract the power of the lens may be increased, causing near-sightedness (myopia), and the gradual yellowing and opacification of the lens may reduce the perception of blue colors. Cataracts typically progress slowly to cause vision loss and are potentially blinding if untreated.

"Fluorescent Marker" as used herein refers to any and all compounds containing fiurophore for attaching the compound to another molecule, such as a protein or nucleic acid. This is generally accomplished using a reactive derivative of the fluorophore that selectively binds to a functional group contained in the target molecule.

"Glaucoma" as used herein refers to a group of diseases that affect the optic nerve and involves a loss of retinal ganglion cells in a characteristic pattern. Glaucoma is categorized as a type of optic neuropathy.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Therapeutically effective amount" as used herein refers to that amount which is capable of achieving beneficial results in a mammal being treated. A therapeutically effective amount can be determined on an individual basis and can be based, at least in part, on consideration of the physiological characteristics of the mammal, the type of delivery system or therapeutic technique used and the time of administration relative to the progression of the disease, disorder or condition being treated.

"Treat," "treating" and "treatment" as used herein refer to both therapeutic treatment and prophylactic or preventative measures, wherein the object is to prevent or slow down (lessen) the targeted pathologic condition, disease or disorder even if the treatment is ultimately unsuccessful. Those in need of treatment may include those already with the disorder as well as those prone to have the disorder or those in whom the disorder is to be prevented.

β-Amyloid deposition is central to AD neuropathology and a key hallmark of Alzheimer's disease. However, monitoring Aβ plaques in the brains of living Alzheimer's patients and animals is limited by the current resolution and specificity of MRI and PET, and a definite diagnosis of Alzheimer's or other ailment or condition characterized by the formation of Aβ plaques is only possible after brain tissue autopsy by monitoring number and distribution of plaques and tangles. Hence, developing means to identify plaques in vivo is essential for diagnosis as well as for evaluation of disease progression in response to therapies.

The present subject matter establishes the formation of retinal Aβ plaques in mammals and teaches a method for identifying, quantizing, and imaging retinal Aβ plaque. The present subject matter may be incorporated for patients with Alzheimer's disease, dementia, and other clinical conditions and ailments characterized by the formation of Aβ plaques.

Furthermore, the present subject matter discovered that the formation of Aβ plaques in the retina of AD patients preceded their appearance in the brain. Accordingly, the present subject matter discloses a method for early diagnosis of AD in a mammal comprising the steps of administering a fluorescent marker to the patient for staining Aβ plaques in the retina, and imaging the retina of the patient with a optical imaging system to identify stained Aβ peptides.

Another embodiment of the present subject matter teaches a method for prognosing AD in mammals by measuring the increase or decrease of Aβ plaques in the retina of patients before and after treatment. The method of prognosis comprises the steps of administering a fluorescent marker to the patient for staining Aβ plaques in the retina and imaging the retina of the patient with an optical imaging system to identify stained Aβ peptides, followed by administering an AD treatment to the patient and allowing due course for the AD treatment to take effect. And, re-administering a fluorescent marker to the patient for staining Aβ plaques in the retina after AD treatment and imaging the retina of the patient with the optical imaging system to identify an increase or decrease in stained Aβ peptides.

In a further embodiment, the present subject matter discloses a method for treating AD in mammalian patients, comprising administering a therapeutically effective amount of myelin-derived peptides and/or agonist of myelin-derived peptides to the patient in reducing the formation of, and dissolving the existence of Aβ plaques.

The present subject matter also finds utility in disclosing methods for improving eyesight in mammalian patients containing retinal Aβ plaques, comprising the steps of administering a therapeutically effective amount of myelin-derived peptides and/or agonist of myelin-derived peptides to the patient. The method of improving eyesight may be applicable for patients with AD, dementia, or other clinical conditions and ailments characterized by the formation of Aβ plaques, such as Age-Related Macular Degeneration (AMD), and glaucoma.

In further embodiments the subject matter describes that Aβ plaques are present in the retina of mammals and may be utilized to analyze, prognose and diagnose a multitude of other clinical conditions and ailments characterized by retinal Aβ plaques. Representative clinical condition and ailments may include AMD and glaucoma.

Further discoveries identified in the present subject matter include an optical imaging system for visualizing Aβ plaques in vivo in the retina of non-human mammalian and human patients. The optical imaging system incorporates the use of a fluorescence microscope, mercury and xenon arc lamps, a CCD camera, an AOTF (acousto-optic tunable filters)-based spectral image acquisition apparatus, and post-analysis imaging software. The optical imaging system incorporates the foregoing tools to provide retinal images of stained Aβ plaques, providing a visual pseudo-color representation of the spectral signature extracted from the raw images, representing the size and location of the Aβ plaques objects.

In an alternative embodiment, the optical imaging system incorporates the use of a stereomicroscope that is adjusted to visualize fluorescence and scatter signals at higher resolutions. The stereomicroscope may be fitted with a Polychrome V variable wavelength light source. In additional embodiments, the optical imaging system may incorporate a MicroFire color digital camera and one or more magnifying lenses to improve magnification and image detail. Image acquisition is attained and perfected by post-analysis image segmentation and classification using imaging software.

In further embodiments, the optical imaging system may be incorporated in methods for diagnosing, prognosing, and treating Aβ plaques in mammals. Furthermore, the optical imaging system may be augmented with adaptive optics, used to improve the performance of the optical imaging system by reducing the effects of rapidly changing optical distortion.

In yet another embodiment, the subject matter method may be utilized for drug development and testing. As the non-invasive, rapidly repetitive imaging methods would enable back-to-back comparison of various drugs and various dosage of drugs, the present subject matter would find favorable utility in drug development and testing.

A previous report has identified Aβ pathology in the brain, based on the finding of Aβ accumulation in the lenses of AD patients [31]. The current study provides evidence for the existence of Aβ plaques in the retinas of AD patients that could be specifically visualized by curcumin. plaques were found in the retina of all examined AD patients, whereas they could not be detected in the non-AD controls. In both young as well as in aged AD mice, a good correlation between retinal and brain Aβ plaque pathology was observed; plaques accumulated in an age-dependent manner during disease progression, and both retina and brain showed Aβ plaque reduction as a response to the same therapeutic modality. Overall, the retinal tissue, which shares many similarities with the brain, can potentially be used for diagnosis and monitoring of AD.

In the present study, Aβ plaques in the retinas of the AD patients were detected mostly within the RGC layer. In AD mouse eyes, plaques were seen in most of the retinal layers and in the choroid. Plaques were noticeable from the NFL to the ONL, and clusters of Aβ plaques were seen more often in the inner layers of the retina, signifying the possibility of plaque imaging through the eyes of living subjects. Retinas of AD mice undergo an age-dependent increase in Aβ plaque load in terms of both number and size, similar to the age-dependent accumulation of plaques observed in the brain. Our results demonstrating retinal plaque pathology are consistent with a recent report that reveals retinal Aβ deposition in correlation with retinal inflammation and degeneration in adult and aged AD-Tg mice [16]. The present subject matter, we not only provides evidence supporting a link between retinal and brain plaque pathology, but also show that Aβ plaques are detectable in the retina prior to their detection in the brain, in young AD-Tg mice. We were further able to show a significant reduction of Aβ plaques in the retinas of AD-Tg mice following vaccination with myelin-derived peptide; this treatment as well as related ones were found to be effective in attenuating Aβ plaque burden in the brain [17, 24, 25]. These findings provide that assessment of retinal plaques may be used to evaluate responses to plaque-reducing therapy, and that retinal plaques may respond to the same treatment that is effective in Aβ plaque reduction in the brain.

Importantly, the fact that plaques were seen in the GCL in the human eyes, reaching a size of more than 5 μm, makes imaging Alzheimer's patients through the retina a feasible approach, with some modifications, even with the currently available tools for human eye imaging, such as an adaptive optics ophthalmoscope [32]. In live mice, a commercially available mydriatic retinal camera, was found to be effective in recording fundus photographs enabling evaluation of longitudinal changes of retinal ganglion cells [33]. A blue-light confocal scanning laser ophthalmoscope (bCSLO) system that was modified to visualize cyan fluorescent protein, also provides a noninvasive approach to visualize RGCs in the living mouse retina [34]. Here, for the proof-of-concept, we were able to detect curcumin-labeled plaques in live mice using a stereomicroscope (Leica S6E) equipped with Polychrome V spectral light source and double convex lens. Moreover, using an AOTF system, we were able to detect retinal Aβ plaques by curcumin while eliminating strong background autofluorescence signals (from red blood cells).

In the present study, curcumin was effective in detecting retinal Aβ plaques when systemically administered at a single dose of 7.5 mg/kg or when given orally. Curcumin demonstrated the ability to cross the blood-brain and blood-retina barriers, which is a requirement for a useful plaque-imaging agent. In terms of safety, Phase I and II trials using curcumin in patients with cancer have proven its low toxicity in humans even at high doses (12 g/day), and when given over extended periods of time [35]. Translation of curcumin doses given intravenously or orally, from mice to humans (below 1 g) for retinal plaque visualization, is expected to remain within the reported safety levels. Furthermore, recent studies have reported various approaches to significantly increase curcumin stability and bioavailability in humans [36].

The identification of Aβ plaques in the retina of AD patients, provides a novel opportunity for developing a high resolution and sensitive imaging method, that will allow their detection in vivo. These results may be consistent with the early visual dysfunctions found in AD patients [37,38], and with the evidence for retinal abnormalities such as loss of cells in the GCL and atrophy of the NFL, reported in AD patients [39-44]. Although it is unclear whether Aβ plaques are found in the retina at early or later stages of AD, the current discovery of Aβ plaques in the retina of these patients at different ages, and the fact that these plaques are detectable at a very early pre-symptomatic phase of the disease in AD-Tg mice, strengthens the possibility that curcumin-labeled plaques, seen through the eyes, could be used for early diagnosis of AD. Importantly, based on their unique size and distribution within the retinas, the plaques observed in AD patients could be eventually used for differential diagnosis: plaques that were detected in age-related macular degeneration are locally restricted to retinal pigment epithelium within drusen and appear smaller in size [45-47]. In terms of the retinal abnormalities seen in AD patients, it is possible that a plaque-reducing therapy, such as the current DC vaccination, may also help to ameliorate some of the visual dysfunctions, even leading to improved eyesight.

Along with aging of the world's population and the growing epidemic of AD, an early detection of AD becomes ever more critical for evaluating risk, assessing new therapies, and treating AD with early intervention once it has developed. AD pathology, including amyloid plaques and neurofibrillary tangles, is believed to appear many years before symptoms manifest and before any substantial neurodegeneration occurs. Discovery of early measurable markers specific to AD, such as the Aβ-plaques in the retina, which may predict development of brain pathology and cognitive decline in still cognitively normal subjects, is especially needed. The inventors' findings in mice models of AD support the use of imaging of retinal plaques in vivo labeled with curcumin as a non-invasive tool for early indication of AD pathology and response to a therapeutic intervention.

Furthermore, the present subject matter introduces vaccination therapies to reduce and/or eliminate Aβ-plaques in the retina, often associated with degeneration of the eyes and eyesight in AD patients. Myelin-derived peptides or weak agonists of myelin-derived peptides were used to effectively induce neuroprotection and to reduce plaque formation in the retina.

In summary, we identified Aβ plaques in human retinas, and describe a new approach to detect and monitor Alzheimer's plaque pathology earlier and more readily than in the brain, by imaging Aβ plaques in the retina using a systemically administered compound, proven safe in humans. This may predict development of brain pathology and cognitive decline in subjects who are still cognitively normal and well before a significant functional deficit is seen. These findings show that optical imaging of the retina can be used as a noninvasive approach for monitoring AD progression and response to therapeutic interventions [48].

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Results

Aβ Deposits in AD Mouse Retina can be Visualized Using Curcumin

Figure 1H:
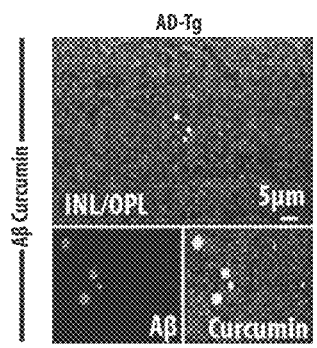
Figure 1I:
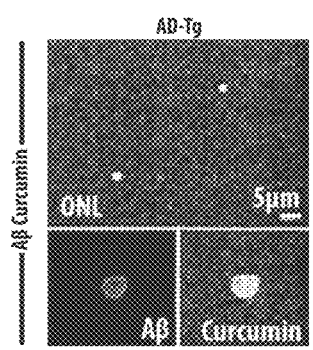
Figure 1J:
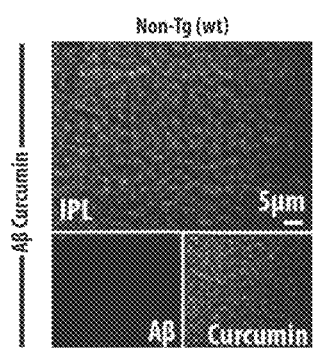
Figure 1K:
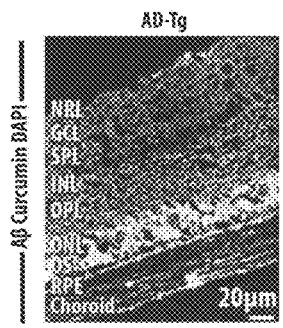
Figure 1L:
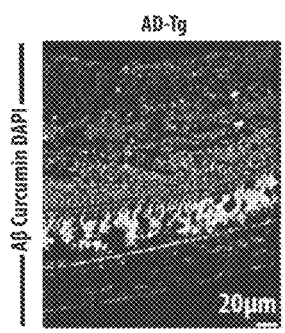
Figure 1M:
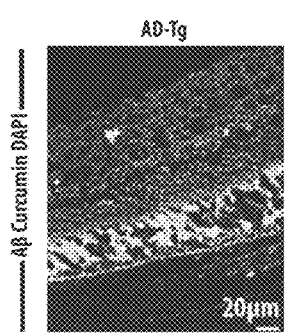
Figure 1N:
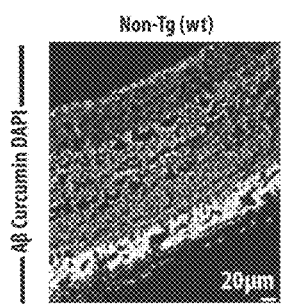

AD-Tg mice carrying the human APPswe and PS1dE9 transgenes were used to assess the potential of developing a noninvasive tool for detecting Aβ plaques in the eye. We first verified that curcumin had an affinity to the same plaques that were detected by antibodies specific to human Aβ in the hippocampus of AD-Tg mice (FIG. 1a; separate channels FIGS. 1b and 1c). At higher magnification, images show the specific staining pattern obtained following each procedure (FIGS. 1d and 1e). Human Aβ-plaques were undetectable in the brains of non-Tg littermate wild type (wt) mice (FIG. 1f). We then tested whether Aβ plaques in the eyes of AD-Tg mice could also bind curcumin. Examination at high resolution revealed the presence of Aβ plaques labeled by both curcumin and anti-human AP-antibodies in the retinas of AD-Tg mice (FIG. 1g retinal whole mount; FIG. 1k-1m, cross-section) but not in the retinas of non-Tg (wt) mice (FIGS. 1j and 1n). The representative images display the location of Aβ plaques in retinal whole mounts at various depths (consecutive acquisition at focal planes of 80 μm depth) to include the inner plexiform layer (IPL; FIG. 1g), inner nuclear layer (INL)/outer plexiform layer (OPL; FIG. 1h), and outer nuclear layer (ONL; FIG. 1i). Analysis of cross sections further verified Aβ plaque deposition in deep retinal layers and the choroid, with an apparent predominance in the ganglion cell layer (GCL) and IPL through OPL layers (FIGS. 1k-1m). Whereas human-Aβ plaques were absent in the non-Tg (wt) littermates (FIGS. 1j and 1n), occasional small curcumin-positive plaques were detected. To determine the nature of these small and sparse plaques that were detected by curcumin staining in wt mice, we carried out a double-staining experiment using curcumin and antibodies specific to mouse-Aβ in wholemount retinas of 10-month old wt mice. Indeed, the small plaques detected by curcumin in the wt retinas were found to be co-labeled with the anti-mouse Aβ antibodies, thus confirming their identity as endogenously formed mouse-Aβ deposits (FIGS. 8a-8d).

Example 2

Results

Figure 2A:
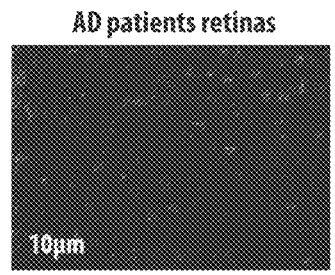
Figure 2B:
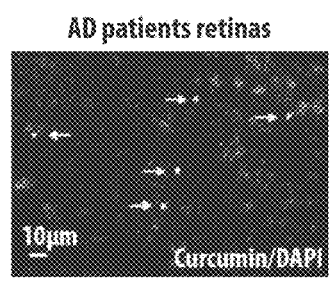
Figure 2C:
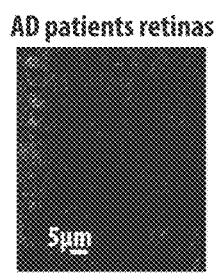
FIGS. 2*c* and 2*d* show higher magnification images of the human whole-mount retina of a 65-yr-old AD patient following Sudan Black B staining (black spots for Sudan staining), and then curcumin staining (curcumin-labeled plaque is indicated by white arrow). Scale bars=5 FIGS. 2*e*-2*g* provide additional examples of curcumin-positive plaques in retinas of a series of 65- to 90-yr-old human AD patients.
Figure 2D:
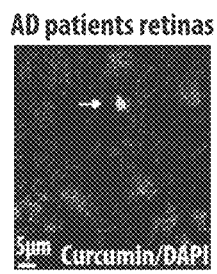
Figure 2E:
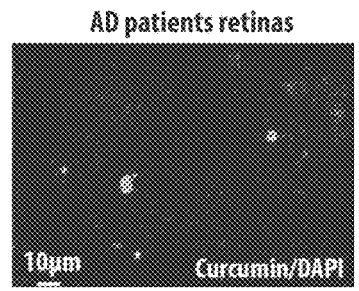
Figure 2F:
Figure 2G:
Figure 2H:
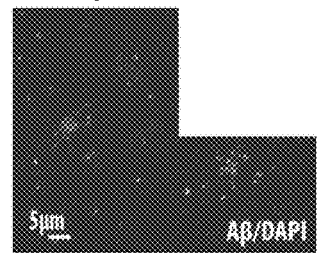
FIGS. 2*h*-2*j* are representative images of human whole-mount retinas of 65- and 87-yr-old human AD patients stained with anti-human Aβ antibodies followed by Sudan Black B treatment at several retinal depths (to include RGC and IPL).
Figure 2I:
Figure 2J:
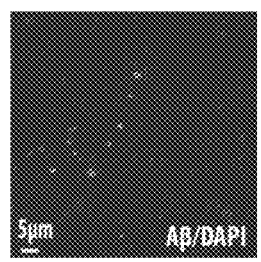

Aβ Plaques are Formed in Retinas of AD Patients and could be Visualized by Curcumin We next examined the presence of Aβ plaques in postmortem eyes of patients with definite diagnosis of AD (n=9; age range from 48 to 94 years; different disease severities, categorized based on their neuropathology reports), and in postmortem eyes of age-matched normal controls (n=4; 66 to 92 years; see human donor eye records in (see Table 1). Autofluorescence and non-specific signals of fixed human eyes observed under excitation ranging from 360-710 nm and associated with lipofuscin/lipid deposits and/or long-term fixation with formalin [21, 22], were eliminated by Sudan Black B staining (FIGS. 2a-2j). For curcumin staining, we first immersed human whole-mount retinas with Sudan Black B (FIGS. 2a and 2c; no plaques were observed), followed by exposure to curcumin (FIGS. 2b and 2d; representative images display plaques within the same tissue location). Plaques detected by curcumin, ranging in size from 1 to 10 μm (typically around 5 μm), were found in all AD patient eyes examined, at various focal depths corresponding to the GCL, IPL and INL retinal layers (FIGS. 2a and 2g), and with an apparent correlation to the reported plaque pathology in the brain. We also analyzed the human retinas with antibodies directed against human Aβ. We identified Aβ plaques in AD patients and found that their structure was similar to that found in the mouse retina and brain [FIGS. 2h and 2i represent the innermost retinal layers (i.e. GCL) where the plaques are easily detected; FIG. 2i is a higher magnification image of the retinal Aβ plaque structure; FIG. 2j represents deeper consecutive focal planes (i.e. IPL)]. The plaques could not be detected when only secondary antibodies were used (data not shown). Exposure of the human retinas to curcumin after their immunolabeling for Aβ, confirmed their co-localization (FIGS. 2k-2m). In non-AD human eyes, no Aβ plaques were detected (FIG. 2n).

TABLE 1

| Patient # | Gender[1] & Age (yrs) | Pre-Mortem Diagnosis (Disease Duration) | Post-Mortem Neuropathology | Final Diagnosis | Cause of Death |
|---|---|---|---|---|---|
| 412 | F, 48 | Dementia, AD (10 yrs) | Moderate to frequent NPs and NFTs in the neocortex and hippocampus | AD definite | Cerebral atrophy with hydrocephalus |
| 404 | F, 65 | Dementia, AD (5 yrs) | Large no. of diffuse plaques, NPs, NFTs in the entorhinal cortex and hippocampus | AD definite | N/A |
| 435 | M, 70 | Dementia, AD (5 yrs) | Moderate no. of NPs and NFTs | AD definite | Pneumonia of posterior lungs |
| 539 | M, 78 | Dementia (3 yrs) | Large no. of NPs most with cores and abundant NFTs and diffuse plaques | AD definite | Subdural hematoma |
| 484 | M, 86 | Dementia, AD (11 yrs) | Abundant NFTs and NPs in the neocortex and hippocampus | AD definite | Cerebrum & Cerebellum infarction |
| 664 | M, 87 | Dementia, AD (8 yrs) | Moderate to frequent NPs with NFTs in the neocortex and Hippocampus CA-1 | AD definite | Cerebrum infraction |
| 486 | F, 88 | Dementia, AD (6 yrs) | Severe NPs and NFTs | AD definite | Pneumonia |
| 513 | F, 90 | Dementia, AD[2] (14 yrs) | Mild NPs[3] and abundant NFTs[4] | AD definite[6] | Cerebral hemorrhage infarction focal |
| 525 | F, 94 | Dementia, AD (11 yrs) | Abundant NPs with mature cores and numerous NDTs | AD definite | Cerebrum infarction |
| 93-78 | M, 66 | Absence of Dementia Normal | N/A | Normal Brain | Liver failure |
| 93-111 | M, 77 | Absence of Dementia Normal | N/A | Normal Brain | Sepsis |
| 476 | M, 88 | Absence of Dementia Occipital CVA[5] | Sparse neocortical NPs and NFTs | Normal Brain | Cerebrum infarctions |
| 529 | F, 92 | Absence of Dementia Normal | Moderate no. of diffuse plaques and small no. of NPs only in the hippocampus | Normal Brain | Cerebrum infarction remote multiple |

[1]Gender: F = Female. M = Male
[2]AD—Alzheimer's Disease
[3]Neuritic Plaques (NPs) and
[4]Neurofibrillary Tangeles (NFTs) were determined by Silver (Galiyas or Bielschowsky) strain and Thioflavin stain in several CNS Sites: Hippocampus CA-1. Entorhinal Cortex. Mid Frontal. Sup./Mid. Temporal. Inferior parietal. Primary Visual. Visual association area.
[5]CVA—Cerebral vascular accident or stroke.
[6]AD definite—According to CERAD criteria.

Example 3

Results

Figure 3A:
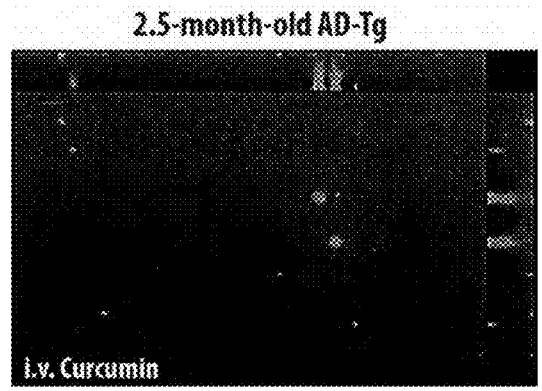
FIGS. 3*a* through 3*q* depict mouse retinal Aβ plaque formations at the pre-symptomatic early stage and accumulation during disease progression. Following i.v. curcumin injections into the tail vein, Aβ plaques were visible in AD-Tg mice retinas and brains.
Figure 3B:
Figure 3C:
Figure 3D:
Figure 3E:
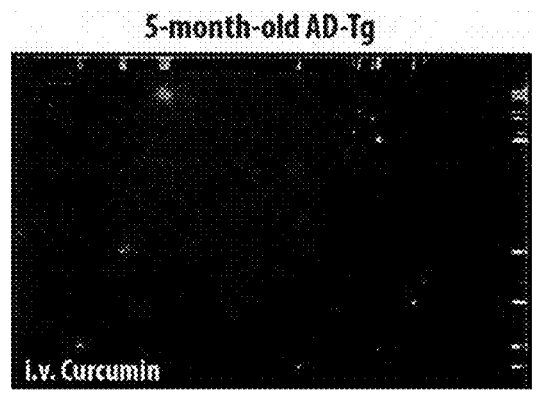
FIGS. 3*e*-3*h* depict 5-month-old AD-Tg mouse, with FIG. 3*e* depicting the presence of plaques in the retina and FIG. 3*f* following specific Aβ antibody staining ex vivo. Scale bars=10 μm.
Figure 3F:
Figure 3G:
Figure 3H:
Figure 3I:
FIGS. 3*i*-3*k* depict 9-month-old AD-Tg mouse, with FIG. 3*i* showing multiple plaques in the retina and FIGS. 3*j* and 3*k* showing plaques in the brain. Scale bars (i)=10 μm and (j,k)=50 μm.
Figure 3J:
Figure 3K:
Figure 3L:
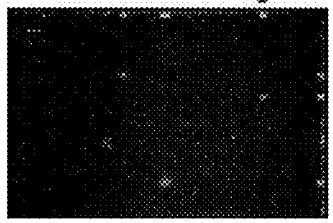
Figure 3M:
Figure 3N:
Figure 3O:
Figure 3P:
Figure 3Q:

Aβ Plaques in AD Mice, Stained In Vivo by Curcumin, are Detected in the Retina Earlier than in the Brain and Accumulate During Disease Progression To establish the use of curcumin for imaging plaques in the retina, we tested its bioavailability to the eye when injected systemically. To this end, mice were intravenously injected with curcumin. Labeled plaques following the administered curcumin could be detected in the retinas and brains of AD-Tg mice, but not in the non-Tg (wt) controls (FIGS. 3a-3q). These findings confirmed that curcumin crosses the blood-brain barrier and suggest that it also crosses the blood-retina barrier and has a high affinity for Aβ plaques in vivo. Importantly, curcumin-labeled plaques could be detected following a single curcumin injection or following multiple injections. Representative z-axis projections of retinal and brain hippocampus and cortical images of AD-Tg mice at the ages of 2.5, 5, 9 and 17 months demonstrated an age-dependent correlation between plaque deposition in the retina and the brain, and increased accumulation over the course of disease progression (FIGS. 3a-3n). Importantly, plaques were detected in the retina (FIGS. 3a and 3b) but not in the brain (FIGS. 3c and 3d) as early as at 2.5 months of age in AD-Tg mice following in vivo curcumin administration, suggesting that Aβ plaques in the retinas precede brain pathology. We further confirmed that these curcumin-labeled plaques were co-localized ex vivo with anti-human Aβ antibody staining (FIGS. 3b and 3f). Aβ plaques were first detectable in the brain at the age of 5 months (FIGS. 3g and 3h), in line with previous descriptions of disease initiation and progression in this strain of AD-Tg mice [23]. In the wt mice, Aβ plaques were undetectable both in the retina (FIG. 3o) and in the brain (FIGS. 3p and 3q) as late as 9 months of age.

Example 4

Results

Aβ Plaque Burden is Decreased in the Retina Following Vaccination Therapy

We further investigated whether the fate of retinal plaques observed in AD-Tg mice, is similar to that of brain Aβ plaques in response to the same treatment. Myelin-derived peptides or weak agonists of myelin-derived peptides have been shown to effectively induce neuroprotection and to reduce plaque formation [24-26]. To ensure the beneficial effect of the vaccination without the risk of inducing autoimmune encephalomyelitis, we chose to vaccinate AD-Tg mice with an altered myelin-derived peptide (MOG45D, derived from MOG 35-5527, 28) using dendritic cells (DCs) as a carrier and adjuvant. Whole-mounted retinas of 10-month old AD-Tg mice injected with either MOG45D-loaded DCs or with PBS, and those of wt littermates (4 mice/8 retinas per group), were ex vivo labeled for Aβ plaques, using both curcumin and anti-Aβ antibody (FIGS. 4a-4k). Representative axial (z-stack) projection images demonstrated substantial reduction of the number of Aβ plaques in vaccinated AD-Tg mice compared to PBS-treated controls (FIGS. 4a-4c versus FIGS. 4d and 4f, respectively; separate channels in FIGS. 4b and 4c, and FIGS. 4e and 4f).

Figure 4I:
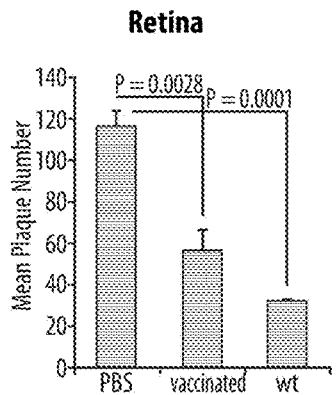
Figure 4J:
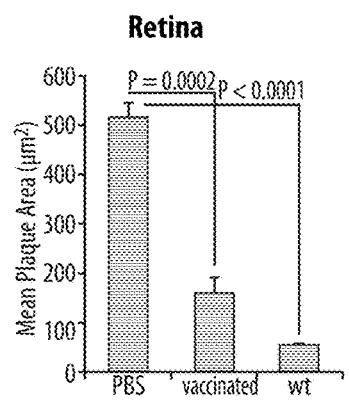
Figure 4K:
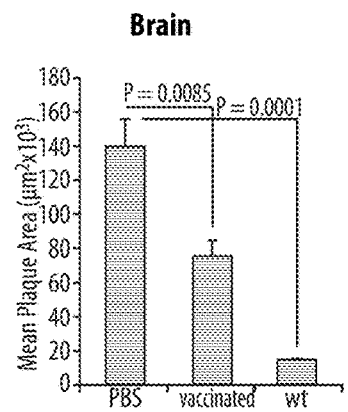

No Aβ plaques (double stained with curcumin and antihuman Aβ antibody) were detected in the wt mice (FIG. 4g). In high-resolution images, we occasionally detected small retinal plaques (mostly<1 μm in diameter), which were found to originate from the endogenous mouse APP gene (FIGS. 8a-8d). These small plaques were stained by curcumin but not by anti-human Aβ antibodies in all three experimental groups (FIGS. 4a, 4d and 4g). We further quantified plaque number and size by capturing 12 areas (total of approx. 0.45 mm$^2$) around the optic disc, and quantified plaques across a 60-μm scanning depth in each area (FIG. 4h; each area is indicated by rectangle 1-12). A significant decrease in plaque number detected by curcumin staining was found in the retinas of vaccinated AD-Tg mice compared to PBS-treated controls (FIG. 4i; P=0.0028). Substantial reduction was also observed in the average area covered by the retinal plaques in vaccinated versus PBS-treated AD-Tg mice (FIG. 3j; P=0.0002). Notably, significant reduction, relative to PBS-treated mice, in the total plaque area was also observed in the hippocampus and cortex from the brains of the same vaccinated mice (FIG. 4k; P=0.0085).

Example 5

Results

Figure 5A:
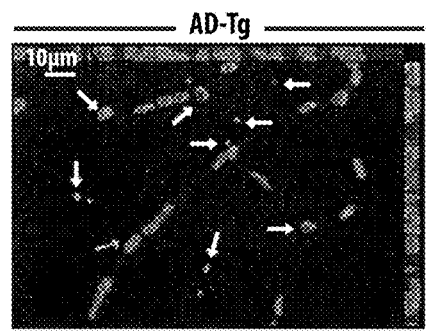
FIGS. 5*a* through 5*k* depict in vivo imaging of curcumin-labeled plaques in AD-Tg mouse retinas.
Figure 5B:
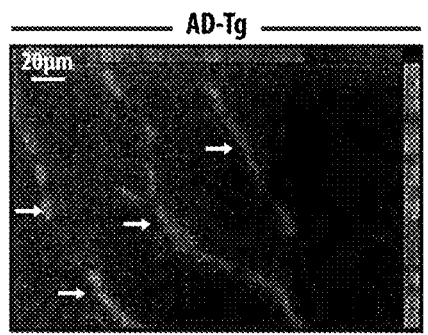
Figure 5C:
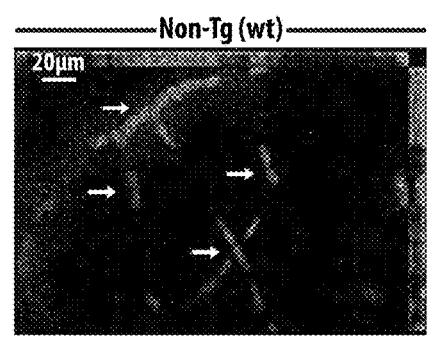
Figure 5D:
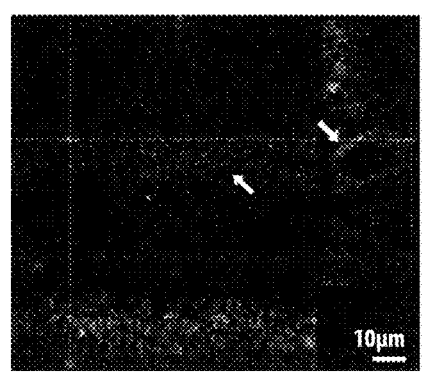
Figure 5E:
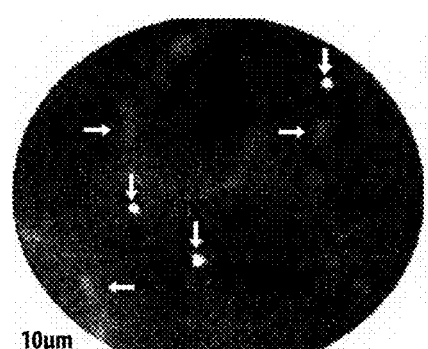
Figure 5F:
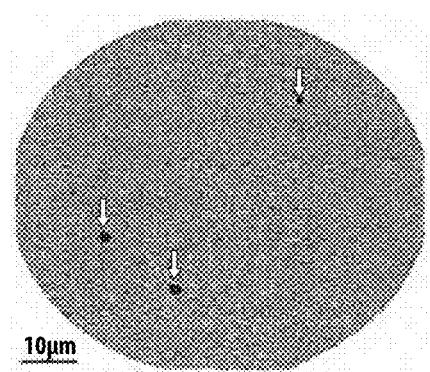
Figure 5H:
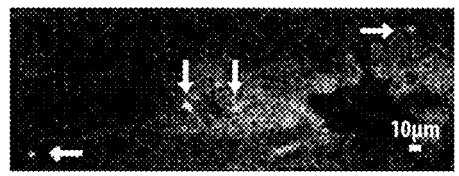
Figure 5G:
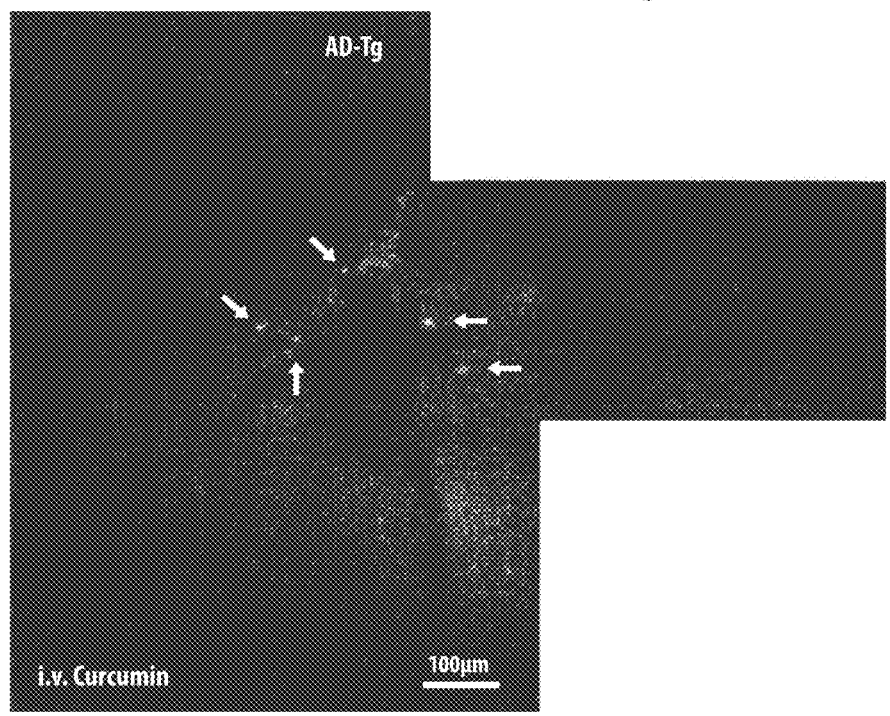
Figure 5I:
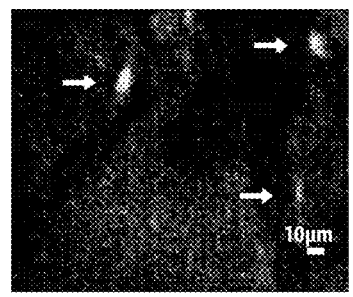
Figure 5J:
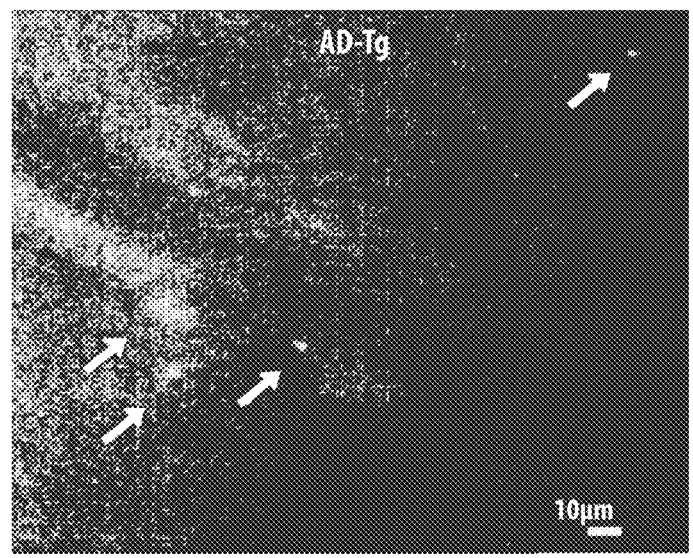
Figure 5K:
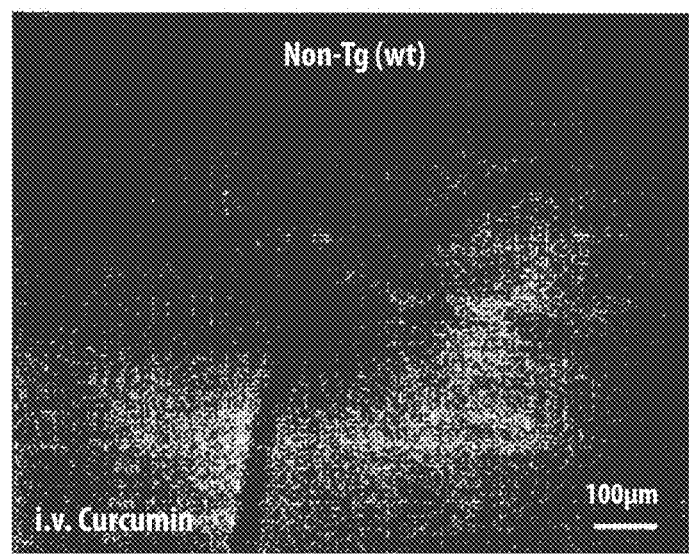

In Vivo Imaging of Aβ Plaques in the Eyes Using Systemically Injected Curcumin To further investigate the potential of visualizing Aβ plaques by curcumin in the eyes of live subjects, we first tested our ability to identify Aβ plaques in whole-mount retinas of mice that were not perfused prior to their eye enucleation, a more physiological setting. Representative axial projection images demonstrated that even under these conditions, which included background signals from red blood cells in the capillaries, plaques could be identified in the retinas of AD-Tg mice that had been previously i.v. injected with curcumin (FIG. 5a). Importantly, in the absence of curcumin, plaques were undetectable in AD-Tg mice that had been i.v. injected with PBS (FIG. 5b), suggesting that when using these imaging modalities, plaques are barely detectable in the retina solely by their autofluorescence signals. As expected, in non-Tg(wt) mice injected with curcumin, plaques were also not detected (FIG. 5c). Additional labeling of plaques with anti-human Aβ antibodies ex vivo, confirmed the Aβ specificity of curcumin staining (data not shown). Aβ plaques in whole-mount retinas of ADTg mice labeled with anti-Aβ antibodies were found inside blood vessels as well as in their parenchymal vicinities (FIG. 5d; confocal virtual cross-section). We further assessed whether it would be possible to detect Aβ plaques while reducing the background signal emerging from blood vessels. To this end, we monitored the specific optical signature using a fluorescence microscope (Nikon TE2000) including a multi-spectral imaging technology, comprised of spectral imaging with acousto-optic tunable filters (AOTF) [29] and fluorescence lifetime imaging using a gated camera; image acquisition was followed by post-analysis image segmentation and classification using software that was previously developed by us [30]. Curcumin-labeled plaques imaged using a microscope equipped with AOTF at a single wavelength channel were observed in AD-Tg mouse retina (FIG. 5e). By applying the AOTF-based imaging, capturing the spectral signature of curcumin-labeled plaques, and post-translation into color-classified digital images, we were able to identify the specific optical signature of Aβ plaques as "true" signals, while eliminating the autofluorescence noise generated by the blood vessels (FIG. 5f). To investigate the feasibility of our approach for noninvasive plaque detection, we conducted an in vivo imaging of the retina in live mice using a modified stereomicroscope (Leica S6E) with a wavelength-controlled light source and a digital camera. Following a single injection of curcumin (7.5 mg/kg) two hours prior to imaging, curcumin-labeled plaques were visible in AD-Tg mice retina specifically at an excitation wavelength of 546/15 nm (FIGS. 5g-5j). Plaques were mostly detected in areas close to the optic disc. The average plaque size was compatible with that observed in the whole-mount retina (ex vivo). No plaques were detected in the non-Tg (wt) mice injected i.v. with curcumin (FIG. 5k) or in AD-Tg mice that did not receive curcumin injection (data not shown). To verify that the signals captured by the modified stereomicroscope originated from the plaques, mice were euthanized, and the presence of the curcumin-labeled plaques was confirmed on whole-mount retinas (data not shown).

Example 6

Mice

Double-transgenic mice (females and males at equal numbers) that harbor the chimeric mouse/human APP (APPswe) and the mutant human presenilin 1 (deletion in exon 9 PSEN1.DELTA.E9) genes and their aged-matched non-Tg littermates, were purchased from the Jackson Laboratories (Bar Harbour, Me., strain #4462) and were bred and maintained in the animal center of comparative medicine of Cedars-Sinai Medical Center (Los Angeles, Calif.). All experiments were approved and conducted according to regulations devised by the Cedars-Sinai Institutional Animal Care and Use Committee.

Example 7

Genotyping

Genomic DNA was extracted from 0.5 cm tail tip using a DNA extraction kit (Qiagen, Valencia, Calif.) following the manufacturer's protocol. Mice used in this study were genotyped for the presence of the transgenes by PCR as previously described (Jankowsky, 2004, Ref #120).

Example 8

Vaccination Preparations

Modified myelin-derived peptide (MOG45D) is derived from the encephalitogenic peptide $MOG_{(35-55)}$ (Koehler, 2002, Ref #285; Shao, 2002, Ref. #283; Zhong, 2002, Ref. #284; Hauben, 2001, Ref. #28; and Hauben, 2001, Ref. #35). For vaccinations, MOG45D (Invitrogen, Carlsbad, Calif.) was added to bone marrow-derived dendritic cells from non-Tg littermates' donor mice. Preparation of dendritic cells for vaccination was as previously described (Hauben, 2003, Ref. #34).

Example 9

Experimental Regimen for Vaccinations

AD-Tg mice at the age of 7 months were injected with DC-MOG45 (0.5×10⁶ cells/200 ml in 1×PBS per animal) once a month, for three months. Control groups of 7-month-old AD-Tg mice were injected with 1×PBS according to the corresponding regimens. At the end of the study, all mice were perfused under anesthesia with 1×PBS following 2.5% paraformaldehyde ("PFA") (Sigma) and their brains and eyes were collected for further analysis.

Example 10

Animal Tissue

Mice were anesthetized and perfused with 4% ice-cold buffered PFA, and a group of mice were not perfused. Their eyes were enucleated and fixed immediately in 4% fresh PFA overnight. For whole mount retinas, the eyes were dissected and the anterior part was removed. The eyecups were soaked for 10 minutes in hyaluronidase (type I-S) (0.07 mg/ml) (Sigma) to liquefy and remove the vitreous residues, than washed for 10 minutes×3 in PBS, and the whole mount retinas were collected. For whole eye sectioning, the eyes were put in 30% sucrose in 4% PFA for 2 hours, than washed for 15 minutes×3 in PBS. The eyes were embedded in O.C.T and frozen slowly on dry ice than sagittal sectioned (7 μm) with cryostat. Brains were collected and fixed immediately in 4% fresh PFA overnight. The brains were put in 30% sucrose (in 4% PFA) gradient. Brains were washed for 15 minutes×3 in PBS, next embedded in O.C.T and frozen slowly on dry ice, then coronal sectioned (30 μm) with cryostat.

Example 11

Human Autopsy Eyes

Autopsy eyes from Alzheimer's patients were procured from the Alzheimer's Disease Research Center, Department of Pathology, University of Southern California (Los Angeles, Calif.), under IRB protocols 99491 and 3201. Healthy donor eyes were purchased from National Disease Research Interchange (NDRI, Philadelphia, Pa.). NDRI has a human tissue collection protocol approved by a managerial committee and subject to National Institutes of Health oversight. Diseased and normal eyes were fixed and stored in 10% neutral buffered formalin. In addition, we used two healthy eyes that were frozen without fixation and stored at −80° C. Whole-mount retinas were prepared from the eyes and further studied by immunohistochemisty.

Example 12

Tail Vein Injection of Curcumin

For in vivo Aβ-plaque imaging, AD-Tg and non-Tg wild-type mice were intravenously injected to the tail vein with curcumin in PBS (7.5 mg/kg/day, for 7 consecutive days) or with PBS. Subsequently, brains and eyes were cryosectioned, or prepared for whole mount retina. In an alternative embodiment, curcumin may be administered to the patient orally.

Example 13

Immunohistochemistry

Brain cryosections (30 μm thick), retina cross sections (cryosections) (7 μm thick) and whole mount retinas were treated with a permeabilization/blocking solution containing 20% horse serum (Invitrogen) and 0.01-0.1% Triton X-100 (Sigma-Aldrich, St. Louis, Mo.). Sections were stained overnight at 4° C. with a specified combination of the following primary Abs in PBS containing 10% blocking solution: mouse anti-Aβ [human amino-acid residues 1-17; clone 6E10 (1:100; Milipore, Temecula, Calif.)]. The sections were incubated for 1 hour in room temperature with secondary Abs, then washed three times with 1×PBS and mounted using Vectorshield containing or not 4',6-diamidino-2-phenylindole, dihydrochloride (DAPI, Vector Laboratories, Peterborough, UK). Secondary Abs solution in 1×PBS contained Cy-5-conjugated donkey anti-mouse antibody (1:200; Jackson ImmunoResearch Laboratories, West Grove, Pa.). A negative control was processed with the same protocol with the omission of the primary antibody to assess nonspecific labeling. For microscopic analysis we used a Zeiss ApoTome fluorescent.

Example 14

Curcumin Staining

Curcumin solution at 0.1 mg/ml was prepared by dissolving curcumin (Sigma-Aldrich) in 0.5M NaOH, pH=7.9, following immediate dilution in 1×PBS. Brain and retina tissue cryosections (30 µm and 7 µm thick respectively) and whole mount retinas were stained with curcumin solution for 10 minutes in room temperature, then rinsed three times with 1×PBS for 15 minutes each. The samples were covered with GVA mounting media (Zymed).

Additional compounds are known in the art that can stain/label in vivo amyloid plaques, including, Thioflavin S and T and some derivatives, Congo Red and derivatives, methoxy-X04, Pittsburgh Compound-B (PiB), DDNP, Chrysamine-G and several more. However, curcumin and it's derivatives are very appealing for in vivo optical imaging of amyloid plaques in animal models as well as humans, because of the following advantage. Curcumin generates specific and very bright signals in the commonly used optical spectrum, and is commercially available, exceptionally low cost. Safety issues related to curcumin are minimal (even at high dosages) and may even consider to be beneficial to the patient's health as an antioxidant. Curcumin is an effective ligand with very good in vitro and in vivo binding characteristics to Aβ, and offers good initial brain uptake and washout rate from the brain (important properties for in vivo imaging agents).

Example 15

Quantification

Micrographs of stained tissues were obtained on an Axio Imager Z1 ApoTome-equipped microscope (with motorized Z-drive) with AxioCam MRm monochrome camera ver. 3.0 (at a resolution of 1388×1040 pixels, 6.45 µm×6.45 µm pixel size, dynamic range of >1:2200, that delivers low-noise images due to Peltier-cooled sensor). Quantitative analysis of Aβ plaque number and area (mm$^2$) was performed from two wholemounted retinas per mouse (n=4 mice per group). Each image, captured at 40× objective with resolution of 0.28 µm, included an area of 0.04 mm$^2$, and a total of 12 rectangular areas around the optic disc within scanning depth of 60 µm (multiple virtual section images at consecutive focal planes using a motorized scanning stage). Measurements of the average plaque radius (following curcumin staining) were completed for each animal group followed by calculation of the average plaque area in each animal group. For the acquisition, we used similar exposure times (approx. 75 ms) and the same gain values (0) for all images. No image post-processing was preformed. The emission signals of Aβplaques stained with curcumin were compared to the background signals in the retinal tissue, to determine signal to background ratio. The calculated signal-to-background noise ratio from the images was high and within the range of 3:1 to 10:1. Quantitative analysis of Aβ plaque number and area (mm$^2$) in the brain was determined from three coronal sections (two hemispheres each) per mouse with 450 µm intervals, over an area covering hippocampal and cortical regions. Optical sections from each field of the specimen were imported into the NIH Image J program (National Institutes of Health). Conversion to greyscale was performed to distinguish between areas of immunoreactivity and background. Total area and quantitative levels of immunoreactivity were determined using a standardized custom histogram-based threshold technique, and then subjected to particle analysis.

Example 16

Spectral and Multispectral Imaging

Spectral imaging provides digital images of an object at a large, sequential number of wavelengths generating precise optical signatures at every pixel. The fluorescence spectral signature of Aβ plaques, labeled in vivo with curcumin, was captured by our spectral imaging system using the following equipment: Nikon fluorescence microscopes (E800 and TE2000), mercury and xenon arc lamps, a CCD camera, an AOTF (acousto-optic tunable filters)-based spectral image acquisition system (ChromoDynamics, Inc)[29] and post-analysis imaging software developed by our Minimally Invasive Surgical Technologies Institute [30]. The final images provided a visual pseudo-color representation of the spectral signature extracted from the raw images, representing the size and location of the analyzed objects. In multispectral imaging, fluorescence lifetime imaging, performed with a pulsed laser and a LaVision PicoStar HR gated camera, was supplementing the spectral acquisition.

Figure 6:
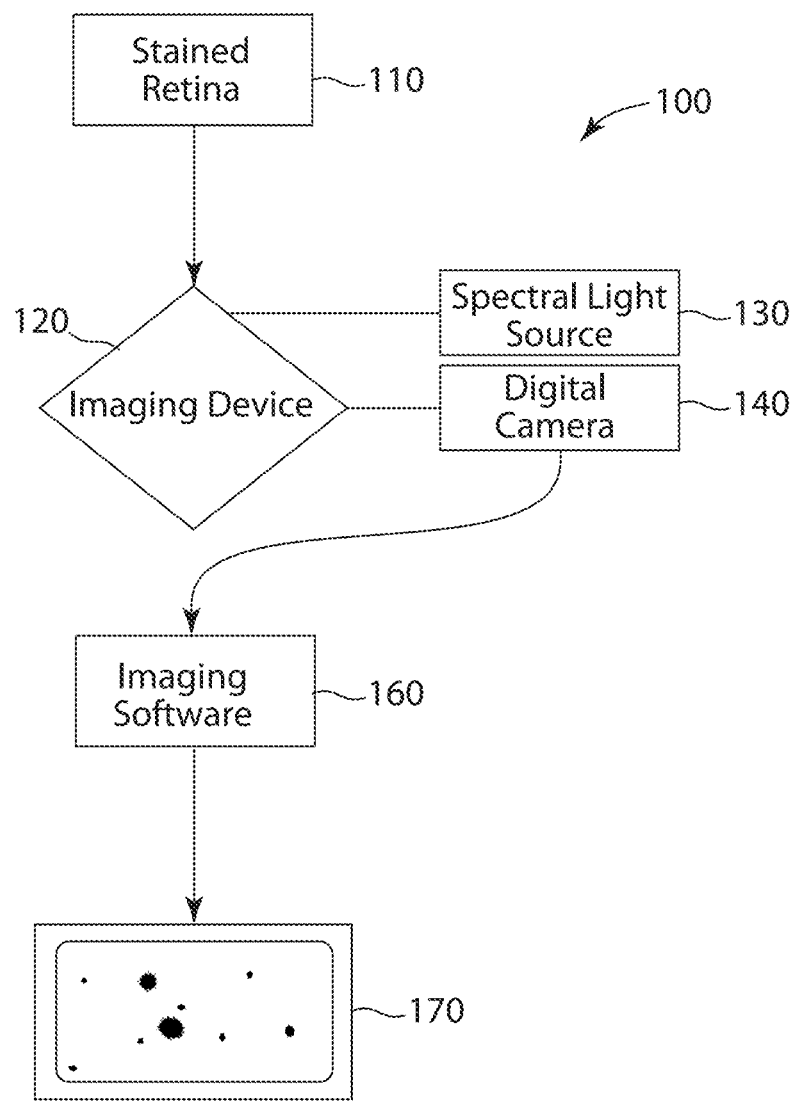
FIG. 6 depicts a flow diagram of a spectral imaging system for diagnosing, prognosing, and analyzing Aβ plaques in accordance with an embodiment of the present invention.

FIG. 6 depicts a flow diagram of a spectral imaging system 100 for diagnosing, prognosing, and analyzing Aβ plaques in vivo in accordance with an embodiment of the present invention. The subject matter retina 110 is stained with a fluorescent marker to label Aβ plaques. Shortly thereafter, the stained retina 110 is imaged by an imaging device 120 that is adjusted to visualize fluorescence and scatter signals at higher resolutions. The imaging device 120 may be fitted with a Polychrome V variable spectral light source 130. In additional embodiments, the spectral imaging system 100 may incorporate a color digital camera 140 (e.g. MicroFire) and one or more magnifying lenses to improve magnification and image detail. Image acquisition 170 is attained by post-analysis image segmentation and classification using imaging software 160.

Figure 7:
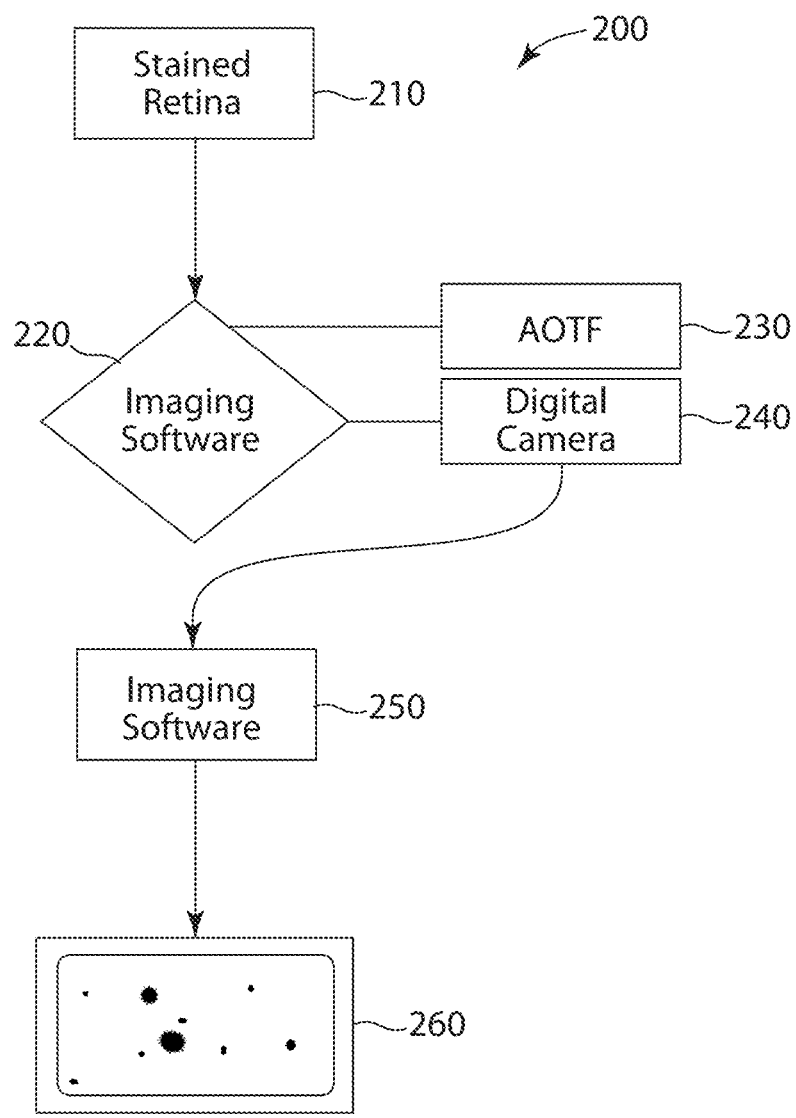
FIG. 7 depicts a flow diagram of a spectral imaging system for diagnosing, prognosing and/or analyzing Aβ plaques in accordance with an embodiment of the present invention.
Figures 8A, 8B:
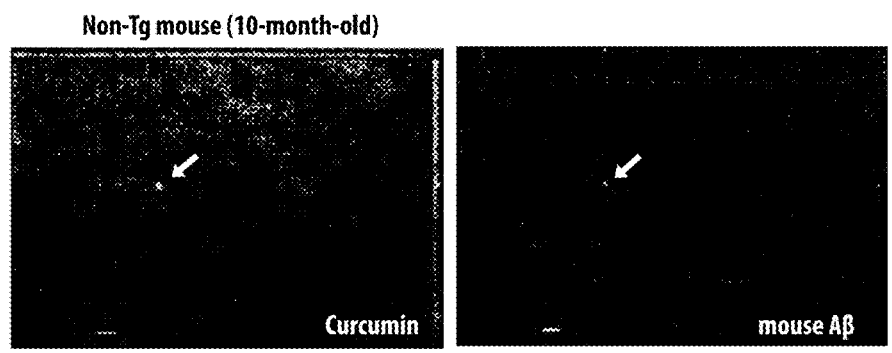
FIGS. 8a through 8d depict high-resolution images of small retinal plaques (mostly<1 µm in diameter), which were found to originate from the endogenous mouse APP gene. Images are of a 10 month old Non-Tg(wt) mouse retina.
Figures 8C, 8D:
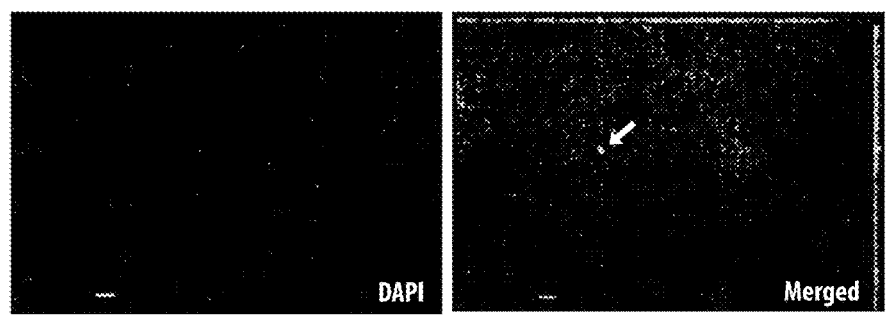
Figure 9:
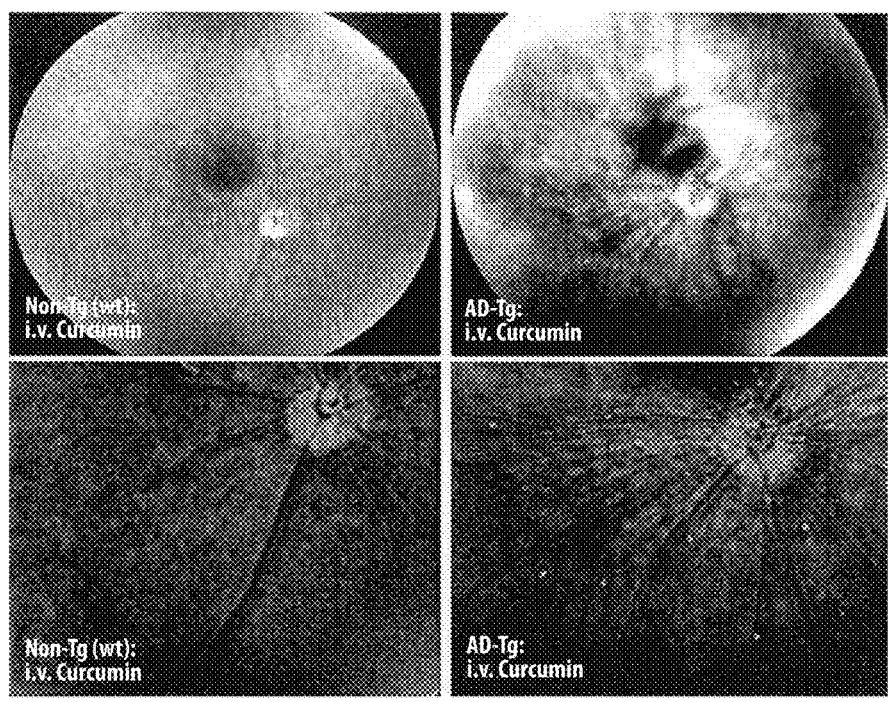
FIG. 9 depicts images of live AD-Tg (upper right and lower right panels) and Non-Tg(wt) (upper left and lower left panels) mouse retinas showing curcumin stained plaques in the AD-Tg retina, and the lack of curcumin stained plaques in the Non-Tg(wt) retina.

FIG. 7 depicts a flow diagram of a spectral imaging system 200 for diagnosing, prognosing, and analyzing Aβ plaques in accordance with an embodiment of the present invention. The subject matter retina 210 is stained with a fluorescent marker to label Aβ plaques. Shortly thereafter, the stained retina 210 is imaged using an imaging device 220. The imaging device 220 may be fitted with multi-spectral imaging technology, comprising of spectral imaging with acousto-optic tunable filters (AOTF) 230 and fluorescence lifetime imaging using a digital camera 240. Image acquisition 260 is attained by post-analysis image segmentation and classification using imaging software 250.

Example 17

In-Vivo Imaging of Mouse Retina

AD-Tg and wt mice retinas were imaged two hours following curcumin intravenous injection. Mice were anaesthetized with Ketamine 100 mg/ml/kg and Xylazine 20 mg/ml/kg. Mouse pupils were dilated to about 2 mm in diameter with 0.5% phenylephrine hydrochloride ophthalmic solution (Bausch & Lomb) combined with 0.5% tropicamide ophthalmic solution (Mydral; Bausch & Lomb). During the imaging process, the mice were positioned on a stage of the stereomicroscope, and the eye was covered with a drop of PBS supplemented with calcium and magnesium, which served as an optical coupling medium between the eye surface and the imaging lens. A modified stereomicroscope (Leica S6E) that was adjusted to visualize fluorescence and scatter signals at higher resolution was used to capture images (exposure time 750 ms. with gain 4). The modified stereomicroscope was assembled to include a Polychrome V (Till Photonics) variable wavelength light source, a MicroFire color digital camera (Optronics), and an additional 6× (double convex) magnifying lens, with a focal length of 10 cm. Images were repeatedly captured at several different angles, in order to visualize a larger field and to eliminate non-specific reflection signals.

Example 18

Statistical Analysis

Results were analyzed by one tailed unpaired Student's t test for the p values of two-group comparison. Results are expressed as means±SD.

Various embodiments of the present subject matter are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the present subject matter known to the applicant at this time of filing the application has been presented and is intended for the purposes of illustration and description. The present description is not intended to be exhaustive nor limit the subject matter to the precise form disclosed and many modifications and variations are possible in the light of the above teachings. The embodiments described serve to explain the principles of the present subject matter and its practical application and to enable others skilled in the art to utilize the subject matter in various embodiments and with various modifications as are suited to the particular use contemplated. Therefore, it is intended that the present subject matter not be limited to the particular embodiments disclosed for carrying out the subject matter.

While particular embodiments of the present subject matter have been shown and described, it will be obvious to those skilled in the art that, based upon the teachings herein, changes and modifications may be made without departing from this subject matter and its broader aspects and, therefore, the appended claims are to encompass within their scope all such changes and modifications as are within the true spirit and scope of this subject matter. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

REFERENCES

1. Sisodia, S. S. & Price, D. L. Role of the beta-amyloid protein in Alzheimer's disease. *FASEB J* 9, 366-370 (1995).
2. Hardy, J. & Selkoe, D. J. The amyloid hypothesis of Alzheimer's disease: progress and problems on the road to therapeutics. *Science* 297, 353-356 (2002).
3. McGeer, P. L. & McGeer, E. G. Local neuroinflammation and the progression of Alzheimer's disease. *J Neurovirol* 8, 529-538 (2002).
4. Klunk, W. E. et al. Imaging brain amyloid in Alzheimer's disease with Pittsburgh Compound-B. *Ann Neurol* 55, 306-319 (2004).
5. Ng, S. et al. Visual assessment versus quantitative assessment of 11C-PIB PET and 18F-FDG PET for detection of Alzheimer's disease. *J Nucl Med* 48, 547-552 (2007).
6. Wang, Y. et al. Development of a PET/SPECT agent for amyloid imaging in Alzheimer's disease. *J Mol Neurosci* 24, 55-62 (2004).
7. Nordberg, A. Amyloid plaque imaging in vivo: current achievement and future prospects. *Eur J Nucl Med Mol Imaging* 35 Suppl 1, S46-50 (2008).
8. Hintersteiner, M. et al. In vivo detection of amyloid-beta deposits by near-infrared imaging using an oxazine-derivative probe. *Nat Biotechnol* 23, 577-583 (2005).
9. Nakada, T., Matsuzawa, H., Igarashi, H., Fujii, Y. & Kwee, I. L. In vivo visualization of senile-plaque-like pathology in Alzheimer's disease patients by MR microscopy on a 7T system. *J Neuroimaging* 18, 125-129 (2008).
10. Toyama, H. et al. PET imaging of brain with the beta-amyloid probe, [11C]6-OHBTA-1, in a transgenic mouse model of Alzheimer's disease. *Eur Nucl Med Mal Imaging* 32, 593-600 (2005).
11. Klunk, W. E. et al. Binding of the positron emission tomography tracer Pittsburgh compound-B reflects the amount of amyloid-beta in Alzheimer's disease brain but not in transgenic mouse brain. *J Neurosci* 25, 10598-10606 (2005).
12. Lockhart, A. et al. PIB is a non-specific imaging marker of amyloid-beta (Abeta) peptide-related cerebral amyloidosis. *Brain* 130, 2607-2615 (2007).
13. Meyer-Luehmarm, M. et al. Rapid appearance and local toxicity of amyloid-beta plaques in a mouse model of Alzheimer's disease. *Nature* 451, 720-724 (2008).
14. Morin, P. J. et al. Amyloid precursor protein is synthesized by retinal ganglion cells, rapidly transported to the optic nerve plasma membrane and nerve terminals, and metabolized. *J Neurochem* 61, 464-473 (1993).
15. Greeve, I. et al. Age-dependent neurodegeneration and Alzheimer-amyloid plaque formation in transgenic *Drosophila*. *J Neurosci* 24, 3899-3906 (2004).

16. Ning, A., Cui, J. Z., To, E., Hsiao Ashe, K. & Matsubara, J. A. Amyloid Beta Deposits Lead to Retinal Degeneration in a Mouse Model of Alzheimer Disease. *Invest Ophthalmol Vis Sci* (2008).
17. Koronyo-Hamaoui, M. et al. Dendritic-cell based vaccination with a weak agonist of myelin-derived peptide attenuates Alzheimer's-like pathology in APP/PS1 transgenic mice. *SfN abstract* 740.1/Q1 (2008).
18. Hauben, E. et al. Vaccination with dendritic cells pulsed with peptides of myelin basic protein promotes functional recovery from spinal cord injury. *J Neurosci* 23, 8808-8819 (2003).
19. Yang, F. et al. Curcumin inhibits formation of amyloid beta oligomers and fibrils, binds plaques, and reduces amyloid in vivo. *J Biol Chem* 280, 5892-5901 (2005).
20. Garcia-Alloza, M., Borrelli, L. A., Rozkalne, A., Hyman, B. T. & Bacskai, B. J. Curcumin labels amyloid pathology in vivo, disrupts existing plaques, and partially 18 restores distorted neurites in an Alzheimer mouse model. *J Neurochem* 102, 1095-1104 (2007).
21. Schnell, S. A., Staines, W. A. & Wessendorf, M. W. Reduction of lipofuscin-like autofluorescence in fluorescently labeled tissue. *J Histochem Cytochem* 47, 719-730 (1999).
22. Baschong, W., Suetterlin, R. & Laeng, R. H. Control of autofluorescence of archival formaldehyde-fixed, paraffin-embedded tissue in confocal laser scanning microscopy (CLSM). *J Histochem Cytochem* 49, 1565-1572 (2001).
23. Garcia-Alloza, M. et al. Characterization of amyloid deposition in the APPswe/PS1dE9 mouse model of Alzheimer disease. *Neurobiol Dis* 24, 516-524 (2006).
24. Frenkel, D., Maron, R., Burt, D. S. & Weiner, H. L. Nasal vaccination with a proteosome-based adjuvant and glatiramer acetate clears beta-amyloid in a mouse model of Alzheimer disease. *J Clin Invest* 115, 2423-2433 (2005).
25. Butovsky, O. et al. Glatiramer acetate fights against Alzheimer's disease by inducing dendritic-like microglia expressing insulin-like growth factor 1. *Proc Natl Acad Sci USA* 103, 11784-11789 (2006).
26. Butovsky, O., Kunis, G., Koronyo-Hamaoui, M. & Schwartz, M. Selective ablation of bone marrow-derived dendritic cells increases amyloid plaques in a mouse Alzheimer's disease model. *Eur J Neurosci* 26, 413-416 (2007).
27. Ford, M. L. & Evavold, B. D. An MHC anchor-substituted analog of myelin oligodendrocyte glycoprotein 35-55 induces IFN-gamma and autoantibodies in the absence of experimental autoimmune encephalomyelitis and optic neuritis. *Eur J Immunol* 34, 388-397 (2004).
28. Ziv, Y., Avidan, H., Pluchino, S., Martino, G. & Schwartz, M. Synergy between immune cells and adult neural stem/progenitor cells promotes functional recovery from spinal cord injury. *Proc Natl Acad Sci USA* 103, 13174-13179 (2006).
29. Wachman, E. S., Niu, W. & Farkas, D. L. AOTF microscope for imaging with increased speed and spectral versatility. *Biophys J* 73, 1215-1222 (1997).
30. Burton, K., Jeong, J., Wachsmann-Hogiu, S, and Farkas, D. L. Spectral optical imaging in biology and medicine in Biomedical Optical Imaging, Edn. In press. (Oxford University Press 2008).
31. Goldstein, L. E. et al. Cytosolic beta-amyloid deposition and supranuclear cataracts in lenses from people with Alzheimer's disease. *Lancet* 361, 1258-1265 (2003).
32. Carroll, J., Choi, S. S. & Williams, D. R. In vivo imaging of the photoreceptor mosaic of a rod monochromat. *Vision Res* 48, 2564-2568 (2008).
33. Murata, H. et al. Imaging mouse retinal ganglion cells and their loss in vivo by a fundus camera in the normal and ischemic-reperfusion model. *Invest Ophthalmol Vis Sci* 49, 5546-5552 (2008).
34. Leung, C. K. et al. Longitudinal profile of retinal ganglion cell damage after optic nerve crush with blue-light confocal scanning laser ophthalmoscopy. *Invest Ophthalmol Vis Sci* 49, 4898-4902 (2008).
35. Dhillon, N. et al. Phase II trial of curcumin in patients with advanced pancreatic cancer. *Clin Cancer Res* 14, 4491-4499 (2008).
36. Anand, P., Kunnumakkara, A. B., Newman, R. A. & Aggarwal, B. B. Bioavailability of curcumin: problems and promises. *Mol Pharm* 4, 807-818 (2007).
37. Sadun, A. A., Borchert, M., DeVita, E., Hinton, D. R. & Bassi, C. J. Assessment of visual impairment in patients with Alzheimer's disease. *Am J Ophthalmol* 104, 113-120 (1987).
38. Katz, B. & Rimmer, S. Ophthalmologic manifestations of Alzheimer's disease. *Surv Ophthalmol* 34, 31-43 (1989).
39. Hinton, D. R., Sadun, A. A., Blanks, J. C. & Miller, C. A. Optic-nerve degeneration in Alzheimer's disease. *N Engl J Med* 315, 485-487 (1986).
40. Blanks, J. C., Torigoe, Y., Hinton, D. R. & Blanks, R. H. Retinal pathology in Alzheimer's disease. I. Ganglion cell loss in foveal/parafoveal retina. *Neurobiol Aging* 17, 377-384 (1996).
41. Trick, G. L., Barris, M. C. & Bickler-Bluth, M. Abnormal pattern electroretinograms in patients with senile dementia of the Alzheimer type. *Ann Neurol* 26, 226-231 (1989).
42. Katz, B., Rimmer, S., Iragui, V. & Katzman, R. Abnormal pattern electroretinogram in Alzheimer's disease: evidence for retinal ganglion cell degeneration? *Ann Neurol* 26, 221-225 (1989).
43. Parisi, V. et al. Morphological and functional retinal impairment in Alzheimer's disease patients. *Clin Neurophysiol* 112, 1860-1867 (2001).
44. Berisha, F., Feke, G. T., Trempe, C. L., McMeel, J. W. & Schepens, C. L. Retinal abnormalities in early Alzheimer's disease. *Invest Ophthalmol Vis Sci* 48, 2285-2289 (2007).
45. Anderson, D. H. et al. Characterization of beta amyloid assemblies in drusen: the deposits associated with aging and age-related macular degeneration. *Exp Eye Res* 78, 243-256 (2004).
46. Dentchev, T., Milam, A. H., Lee, V. M., Trojanowski, J. Q. & Dunaief, J. L. Amyloidbeta is found in drusen from some age-related macular degeneration retinas, but not in drusen from normal retinas. *Mol Vis* 9, 184-190 (2003).
47. Ding, J. D. et al. Targeting age-related macular degeneration with Alzheimer's disease based immunotherapies: anti-amyloid-beta antibody attenuates pathologies in an agerelated macular degeneration mouse model. *Vision Res* 48, 339-345 (2008).
48. Koronyo, Y., Koronyo-Hamaoui, M., Black, K. L., Schwartz, M. & Farkas, D. L., Optical method for the detection of Alzheimer's Disease. Patent application submitted to the USPTO (2008)
49. Jankowsky, J. L. et al. APP processing and amyloid deposition in mice haploinsufficient for presenilin 1. *Neurobiol Aging* 25, 885-892 (2004).

50. McKinnon S J, Lehman D M, Kerrigan-Baumrind L A, Merges C A, Pease M E, Kerrigan D F, Ransom N L, Tahzib N G, Reitsamer H A, Levkovitch-Verbin H, et al. (2002) *Invest Ophthalmol Vis Sci* 43, 1077-1087.

51. Yoneda S, Hara H, Hirata A, Fukushima M, Inomata Y, & Tanihara H (2005) *Jpn J Ophthalmol* 49, 106-108.

52. Guo L, Salt T E, Luong V, Wood N, Cheung W, Maass A, Ferrari G, Russo-Marie F, Sillito A M, Cheetham M E, et al. (2007) *Proc Natl Acad Sci USA* 104, 13444-13449.

53. Dentchev T, Milam A H, Lee V M, Trojanowski J Q, & DunaiefJ L (2003) *Mol Vis* 9, 184-190.

What is claimed is:

1. A method for diagnosing Alzheimer's disease in vivo in a human subject, comprising systemically administering curcumin to the subject for staining retinal Aβ plaques; imaging the subject's retina with an optical imaging system suitable for visualizing retinal Aβ plaques of from 1 μm to 10 μm; examining the images for stained retinal Aβ plaques of from 1 μm to 10 μm; and diagnosing the subject as having Alzheimer's disease if stained retinal Aβ plaques of from 1 μm to 10 μm are present.

2. The method of claim 1, wherein stained retinal Aβ plaques are present in the ganglion cell layer (GCL), inner plexiform layer (IPL) and inner nuclear layer (INL) of the subject's retina.

3. The method of claim 1, wherein stained retinal Aβ plaques are present in the ganglion cell layer (GCL) of the subject's retina.

4. The method of claim 1, wherein the optical imaging system is selected from the group consisting of a spectrometer, a fluorescence microscope, a stereomicroscope, a mercury arc lamp, a variable wavelength light source, a xenon arc lamp, a CCD gated camera, a color digital camera, an acoustic-optic tunable filter-based spectral image acquisition system, adaptive optics, imaging software, and combinations thereof.

5. The method of claim 1, wherein the amount of curcumin administered is less than 12.0 grams and greater than 7.5 mg.

6. A method for diagnosing Alzheimer's disease in vivo in a human subject, comprising systemically administering curcumin to the subject for staining retinal Aβ plaques; imaging the subject's retina with an optical imaging system suitable for visualizing retinal Aβ plaques of more than 5 μm; examining the image for stained retinal Aβ plaques of more than 5 μm; and diagnosing the subject as having Alzheimer's disease if stained retinal Aβ plaques of more than 5 μm are present.

7. The method of claim 6, wherein stained retinal Aβ plaques are present in the ganglion cell layer (GCL), inner plexiform layer (IPL) and inner nuclear layer (INL) of the subject's retina.

8. The method of claim 6, wherein stained retinal Aβ plaques are present in the ganglion cell layer (GCL) of the subject's retina.

9. The method of claim 6, wherein the optical imaging system is selected from the group consisting of a spectrometer, a fluorescence microscope, a stereomicroscope, a mercury arc lamp, a variable wavelength light source, a xenon arc lamp, a CCD gated camera, a color digital camera, an acoustic-optic tunable filter-based spectral image acquisition system, adaptive optics, imaging software, and combinations thereof.

10. The method of claim 6, wherein the amount of curcumin administered is less than 12.0 grams and greater than 7.5 mg.

11. A method for identifying Aβ plaques in a human subject's retina in vivo, comprising systemically administering curcumin to the subject for staining retinal Aβ plaques; imaging the subject's retina with an optical imaging system suitable for visualizing retinal Aβ plaques of from 1 μm to 10 μm; and examining the image for stained retinal Aβ plaques of from 1 μm to 10 μm.

12. The method of claim 11, wherein stained retinal Aβ plaques are present in the ganglion cell layer (GCL), inner plexiform layer (IPL) and inner nuclear layer (INL) of the subject's retina.

13. The method of claim 11, wherein stained retinal Aβ plaques are present in the ganglion cell layer (GCL) of the subject's retina.

14. The method of claim 11, wherein the optical imaging system is selected from the group consisting of a spectrometer, a fluorescence microscope, a stereomicroscope, a mercury arc lamp, a variable wavelength light source, a xenon arc lamp, a CCD gated camera, a color digital camera, an acoustic-optic tunable filter-based spectral image acquisition system, adaptive optics, imaging software, and combinations thereof.

15. The method of claim 11, wherein the amount of curcumin administered is less than 12.0 grams and greater than 7.5 mg.

16. A method for identifying Aβ plaques in a human subject's retina in vivo, comprising systemically administering curcumin to the subject for staining retinal Aβ plaques; imaging the subject's retina with an optical imaging system suitable for visualizing retinal Aβ plaques of more than 5 μm; and examining the image for stained retinal Aβ plaques of more than 5 μm.

17. The method of claim 16, wherein stained retinal Aβ plaques are present in the ganglion cell layer (GCL), inner plexiform layer (IPL) and inner nuclear layer (INL) of the subject's retina.

18. The method of claim 16, wherein stained retinal Aβ plaques are present in the ganglion cell layer (GCL) of the subject's retina.

19. The method of claim 16, wherein the optical imaging system is selected from the group consisting of a spectrometer, a fluorescence microscope, a stereomicroscope, a mercury arc lamp, a variable wavelength light source, a xenon arc lamp, a CCD gated camera, a color digital camera, an acoustic-optic tunable filter-based spectral image acquisition system, adaptive optics, imaging software, and combinations thereof.

20. The method of claim 16, wherein the amount of curcumin administered is less than 12.0 grams and greater than 7.5 mg.

* * * * *